US006821370B2

(12) United States Patent
Tomsovic et al.

(10) Patent No.: US 6,821,370 B2
(45) Date of Patent: Nov. 23, 2004

(54) METHOD FOR POSITIONING GARMENT SIDE PANELS

(75) Inventors: Charles Robert Tomsovic, Omro, WI (US); Kurt Garrett Krupka, Neenah, WI (US); David Albert Maxton, Menasha, WI (US); Robert Lee Popp, Hortonville, WI (US); Michael William Protheroe, Neenah, WI (US); Timothy Alan Thorson, Appleton, WI (US); Brian Robert Vogt, Oshkosh, WI (US); Michael John Wanner, Appleton, WI (US); Thomas Earl Williamson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 289 days.

(21) Appl. No.: 10/010,110

(22) Filed: Nov. 13, 2001

(65) Prior Publication Data

US 2003/0089453 A1 May 15, 2003

(51) Int. Cl.⁷ .............................................. A41H 43/04
(52) U.S. Cl. ....................... 156/200; 156/202; 156/204; 156/217; 156/226; 156/227; 604/385.3; 604/390; 493/450
(58) Field of Search .................................. 156/200–202, 156/204, 217, 226, 227; 604/385.201, 385.3, 385.21, 390; 271/7, 264; 493/416, 418, 423, 450

(56) References Cited

U.S. PATENT DOCUMENTS

| 4,145,763 A | 3/1979 | Abrams et al. |
| 4,205,679 A | 6/1980 | Repke et al. |
| 4,402,690 A | 9/1983 | Redfern |
| 4,610,680 A | 9/1986 | LaFleur |
| 4,615,695 A | 10/1986 | Cooper |
| 4,663,220 A | 5/1987 | Wisneski et al. |
| 4,699,622 A | 10/1987 | Toussant et al. |
| 4,701,156 A | 10/1987 | Larsonneur |
| 4,704,116 A | 11/1987 | Enloe |
| 4,940,464 A | 7/1990 | Van Gompel et al. |
| 5,046,272 A | 9/1991 | Vogt et al. |
| 5,087,253 A | 2/1992 | Cooper |
| 5,104,116 A | 4/1992 | Pohjola |
| 5,110,403 A | 5/1992 | Ehlert |
| 5,224,405 A | 7/1993 | Pohjola |
| 5,226,992 A | 7/1993 | Morman |
| 5,370,634 A | 12/1994 | Ando et al. |
| 5,660,666 A | 8/1997 | Dilnik et al. |
| 5,766,389 A | 6/1998 | Brandon et al. |
| 5,779,831 A | 7/1998 | Schmitz |
| 5,785,699 A | 7/1998 | Schmitz |

(List continued on next page.)

FOREIGN PATENT DOCUMENTS

| EP | 0 217 032 B1 | 2/1992 |
| EP | 0 757 550 B1 | 12/1998 |
| GB | 1 520 740 | 8/1978 |
| WO | WO 95/27462 A1 | 10/1995 |
| WO | WO 00/23025 A1 | 4/2000 |
| WO | WO 00/35398 A1 | 6/2000 |
| WO | WO 00/37009 | 6/2000 |
| WO | WO 01/87753 A2 | 11/2001 |

*Primary Examiner*—Sam Chaun Yao
(74) *Attorney, Agent, or Firm*—Thomas M. Gage; John L. Brodersen

(57) ABSTRACT

A method for positioning side panels during manufacture of a pant includes positioning the side panels within fluid flow devices. The side panels can move parallel or perpendicular to a pant transport plane as the pant is transported in the machine direction and the side panels reside within the fluid flow devices. The side panels can include refastenable fastening components. The method and apparatus can move the fastening components closer together in the cross-machine direction while the side panels reside within the fluid flow devices.

22 Claims, 33 Drawing Sheets

U.S. PATENT DOCUMENTS

| | | | |
|---|---|---|---|
| 5,795,350 | A | 8/1998 | Schmitz |
| 5,830,206 | A | 11/1998 | Larsson |
| 5,855,574 | A | 1/1999 | Kling et al. |
| 5,858,515 | A | 1/1999 | Stokes et al. |
| 5,897,545 | A | 4/1999 | Kline et al. |
| 6,264,784 | B1 | 7/2001 | Menard et al. |
| 6,287,287 | B1 | 9/2001 | Elsberg |
| 6,328,725 | B2 | 12/2001 | Fernfors |
| 6,395,115 | B1 | 5/2002 | Popp et al. |
| 6,409,858 | B1 | 6/2002 | Popp et al. |
| 6,432,243 | B1 | 8/2002 | Popp et al. |
| 6,432,248 | B1 | 8/2002 | Popp et al. |
| 6,447,628 | B1 | 9/2002 | Couillard et al. |
| 6,461,344 | B1 | 10/2002 | Widlund et al. |
| 6,481,362 | B2 | 11/2002 | Hietpas et al. |
| 6,497,032 | B2 | 12/2002 | Maxton et al. |
| 6,513,221 | B2 | 2/2003 | Vogt et al. |
| 6,514,187 | B2 | 2/2003 | Coenen et al. |
| 6,562,167 | B2 | 5/2003 | Coenen et al. |
| 6,596,113 | B2 * | 7/2003 | Csida et al. ............ 156/217 |

* cited by examiner

METHOD FOR POSITIONING GARMENT SIDE PANELS

BACKGROUND OF THE INVENTION

The present invention pertains to processes and apparatus for making garments, and more particularly to processes and apparatus for making prefastened and refastenable garments.

Garments such as disposable absorbent garments have numerous applications including diapers, training pants, feminine care products, and adult incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

Manufacturing techniques for making conventional garments are in some respects inadequate for making new product forms, such as prefastened and refastenable garments. Hence, what is lacking and needed in the art are processes and apparatus for making garments, and in particular for making prefastened and refastenable garments such as disposable absorbent garments.

SUMMARY OF THE INVENTION

In response to the above-referenced unfulfilled need in the art, new processes and apparatus for making garments have been discovered. In one aspect, the invention concerns a method for positioning side panels during manufacture of a pant. An embodiment of the method comprises transporting a pant in a machine direction thus defining a pant transport plane and a z-direction perpendicular to the pant transport plane. The pant can comprise at least one waist region having opposite side panels. The method also comprises positioning the side panels within fluid flow devices, where each fluid flow device defines a side panel transport path which is disposed at an angle with respect to the pant transport plane. In this way, the side panels can move in the z-direction while the pant is transported in the machine direction and the side panels reside within the fluid flow devices.

Another embodiment of the method for positioning side panels during manufacture of a pant comprises transporting a pant in a machine direction thus defining a pant transport plane and a z-direction perpendicular to the pant transport plane. The pant can comprise at least one waist region comprising opposite side panels. In this embodiment, the side panels are positioned within fluid flow devices located on opposite sides of a machine center line. Each fluid flow device is oriented at an angle with respect to the pant transport plane such that at least laterally outward portions of the side panels move in the z-direction and toward the machine center line while the pant is transported in the machine direction and the side panels reside within the fluid flow devices.

The z-direction movement can be useful in many embodiments, but may be particularly useful where the side panels include fastening components and it is desired to move the fastening components closer together in the transverse direction. For instance, the fastening components can be positioned closer together by creating an elevation difference between portions of the waist region containing the fastening components and another portion of the waist region. In particular embodiments, the fastening components can be disposed in the side panels, and the absorbent chassis and/or side panels can be repositioned to create an elevation difference between at least a portion of the absorbent chassis and the side panels.

In some embodiments of the present method, at least portions of the side panels are allowed to move inward toward the machine center line while the pant is transported in the machine direction and the side panels reside within the fluid flow devices. This inward movement can be useful in preparing the side panels for attachment to the opposite waist region. At other points in the process which are described in greater detail below, the side panels can be maintained at a constant cross-machine direction position while the pant is transported in the machine direction.

Hence, another aspect of the invention concerns methods for making prefastened and refastenable pants. An embodiment of the method comprises transporting a folded pant in a machine direction thus defining a pant transport plane and a z-direction perpendicular to the pant transport plane. The folded pant can have opposite first and second waist regions in facing relation, with the first waist region comprising first side panels and the second waist region comprising second side panels. The first side panels can comprise initially inward-facing fastening components and the second side panels can comprise initially outward-facing fastening components. The method includes inverting the initially outward-facing fastening components. Additionally, the first side panels are transported within fluid flow devices in the z-direction away from the pant transport plane while the folded pant is transported in the machine direction. The first side panels can be transferred from the fluid flow devices to side panel transfer devices, upon which the first side panels can be transported on the side panel transfer devices in the z-direction toward the pant transport plane while the folded pant is transported in the machine direction. The initially inward-facing and initially outward-facing fastening components can then be engaged with one another.

In particular embodiments, the initially inward-facing fastening components can be separated from one another by an initial distance and the initially outward-facing fastening components can be separated from one another by substantially the same initial distance. In the context of the present invention, the distance between initially inward-facing fastening components and the distance between the initially outward-facing fastening components both refer to the transverse linear distance between the fastening components. "Transverse linear distance" is used herein to refer to the distance between two fastening components, measured in a straight line parallel to the transverse axis of the garment without regard to surface contours of the garment. There may or may not be any force exerted in the transverse direction at the time of measurement.

Fluid flow devices as described herein can also be oriented parallel to the pant transport plane. Such parallel fluid flow devices can be employed to transport the side panels in the machine direction while portions of the side panels are disposed at z-direction positions displaced from the pant transport plane. Parallel fluid flow devices can reduce friction and assist in straightening the side panels. Hence, in another embodiment, a method for positioning side panels during manufacture of a pant comprises: transporting a pant in a machine direction thus defining a pant transport plane and a z-direction perpendicular to the pant transport plane, the pant comprising at least one waist region comprising opposite side panels; transporting at least laterally outward portions of the side panels in the z-direction away from the pant transport plane while the pant is transported in the machine direction; positioning the side panels within internal passageways of fluid flow devices located on opposite sides of a machine center line, the internal passageways displaced in the z-direction outside the pant transport plane; and transporting the side panels within the internal passageways while at least laterally outward portions of the side panels reside outside the pant transport plane and the pant is transported in the machine direction.

In a further embodiment, a method for positioning side panels during manufacture of a pant comprises: transporting a pant in a machine direction thus defining a pant transport plane and a z-direction perpendicular to the pant transport plane, the pant comprising at least one waist region comprising opposite side panels; positioning the side panels within fluid flow devices located on opposite sides of a machine center line, each fluid flow device comprising walls defining an internal passageway, an entry slot to the internal passageway disposed toward the machine center line, and a fluid discharge region opposite the entry slot, the walls extending in the machine direction; creating a flow of fluid through each internal passageway from the entry slot toward the fluid discharge region; and transporting the side panels in the machine direction within the fluid flow devices while at least laterally outward portions of the side panels are displaced in the z-direction from the pant transport plane.

A further aspect concerns an apparatus for making garments. In particular embodiments, the apparatus comprises first and second conveyors adapted to transport a stream of discrete, partially assembled and folded pants sandwiched between the conveyors in a machine direction. The conveyors define a machine center line and a pant transport plane. Fluid flow devices, which are disposed transversely outward from the machine center line, each define a side panel transport path disposed at an angle to the pant transport plane.

In another embodiment, the apparatus comprises first and second conveyors adapted to transport a stream of discrete, partially assembled and folded pants sandwiched between the conveyors in a machine direction. The conveyors define a machine center line, a pant transport plane, and a z-direction perpendicular to the pant transport plane. The apparatus also comprises fluid flow devices transversely outward from the machine center line. Each fluid flow device defines an internal passageway, an entry slot to the internal passageway disposed toward the machine center line, and a fluid discharge region opposite the entry slot. Each internal passageway defines a reference surface that is displaced from the pant transport plane in the z-direction such that the internal passageways reside outside the pant transport plane. The amount of the displacement will vary depending upon the particular application and machine configuration. For example, each reference surface can be displaced from the pant transport plane in the z-direction by greater than 0 millimeters and less than about 50 millimeters, particularly by greater than about 10 millimeters and less than about 25 millimeters.

The terms "air" and "fluid" are used interchangeably herein to refer to any gaseous substance, for example, air at ambient temperature. Where the specific application permits, the term "fluid" also includes any liquid medium.

The processes and apparatus described herein can be useful in making a wide variety of garments. The waist regions of such garments can have the same transverse width dimensions or have different width dimension. Moreover, the processes and apparatus can be applied to one or both waist regions. Accordingly, the term "first waist region" can correspond to either the front or the back waist region.

The garment can be folded in half through the crotch region by a variety of mechanisms. It may be desirable to maintain separation of the side panels and separation of the fastening components while the product is folded in half. The fastening components can be engaged simultaneously or sequentially with folding of the pant.

The fastening components can comprise separate elements bonded to another component of the pant. Alternatively, the fastening components can comprise a portion of another element of the pant, such as the bodyside liner, the outer cover, separate side panels if employed, integral side panels if employed, a belt-type component extending transversely across the chassis if employed, or the like. Thus, unless otherwise specified, the term "fastening component" includes both separate components which function as fasteners and regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

A refastenable fastening system allows for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing.

The present invention can be used in the manufacture of a wide variety of absorbent and non-absorbent products, including training pants, swim pants, diaper pants, incontinence garments, feminine care products, health care garments, apparel for institutional, industrial and consumer use, or other garments. Absorbent articles are adapted to be worn adjacent to the body of a wearer to absorb and contain various exudates discharged from the body. The absorbent articles can be prefastened to provide a pant-like product for the user. The product can then be pulled on like a conventional training pant, and subsequently checked or removed with the ease of a diaper-like product. Moreover, the product may be applied like a diaper rather than like a pant.

Supplemental releasable fastening means such as frangible point bonds may be employed to maintain the absorbent article in a pant configuration until the user intentionally disengages the fasteners.

Particular training pants suitable for use with the present invention are disclosed in U.S. patent application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams;" which is incorporated herein by reference. This reference describes various materials and methods for constructing training pants. Training pants can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; which are also incorporated herein by reference.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to make a variety of garments. Examples of such garments include disposable absorbent articles such as diapers, training pants, feminine hygiene products, incontinence products, other personal care or health care garments; swim pants; athletic clothing; pants and shorts; or the like. For ease of explanation, the description hereafter will be in terms of methods and apparatus for making a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference.

Figure 1:
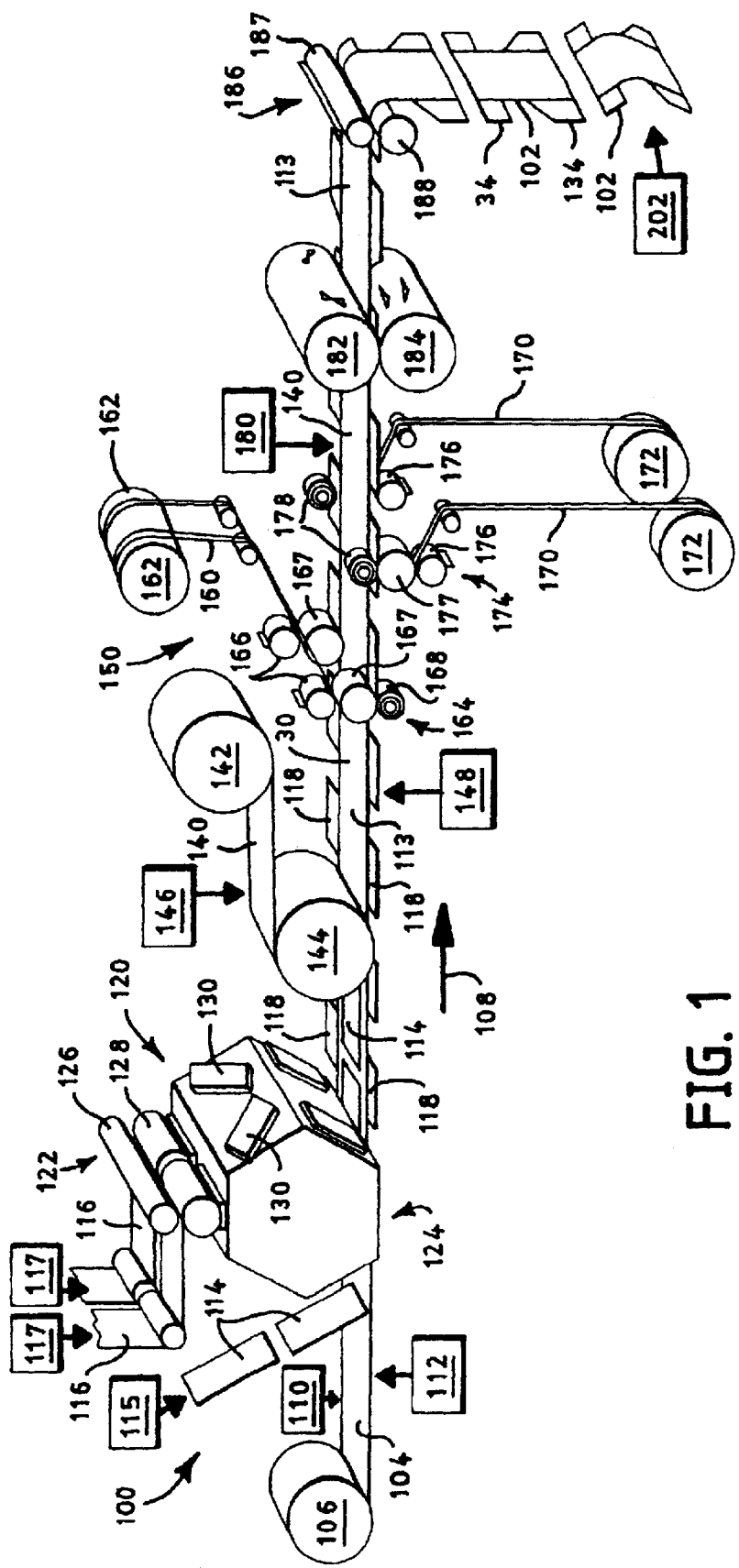
FIG. 1 is a schematic view of an exemplary embodiment of an assembly section for making garments such as training pants.
Figure 2:
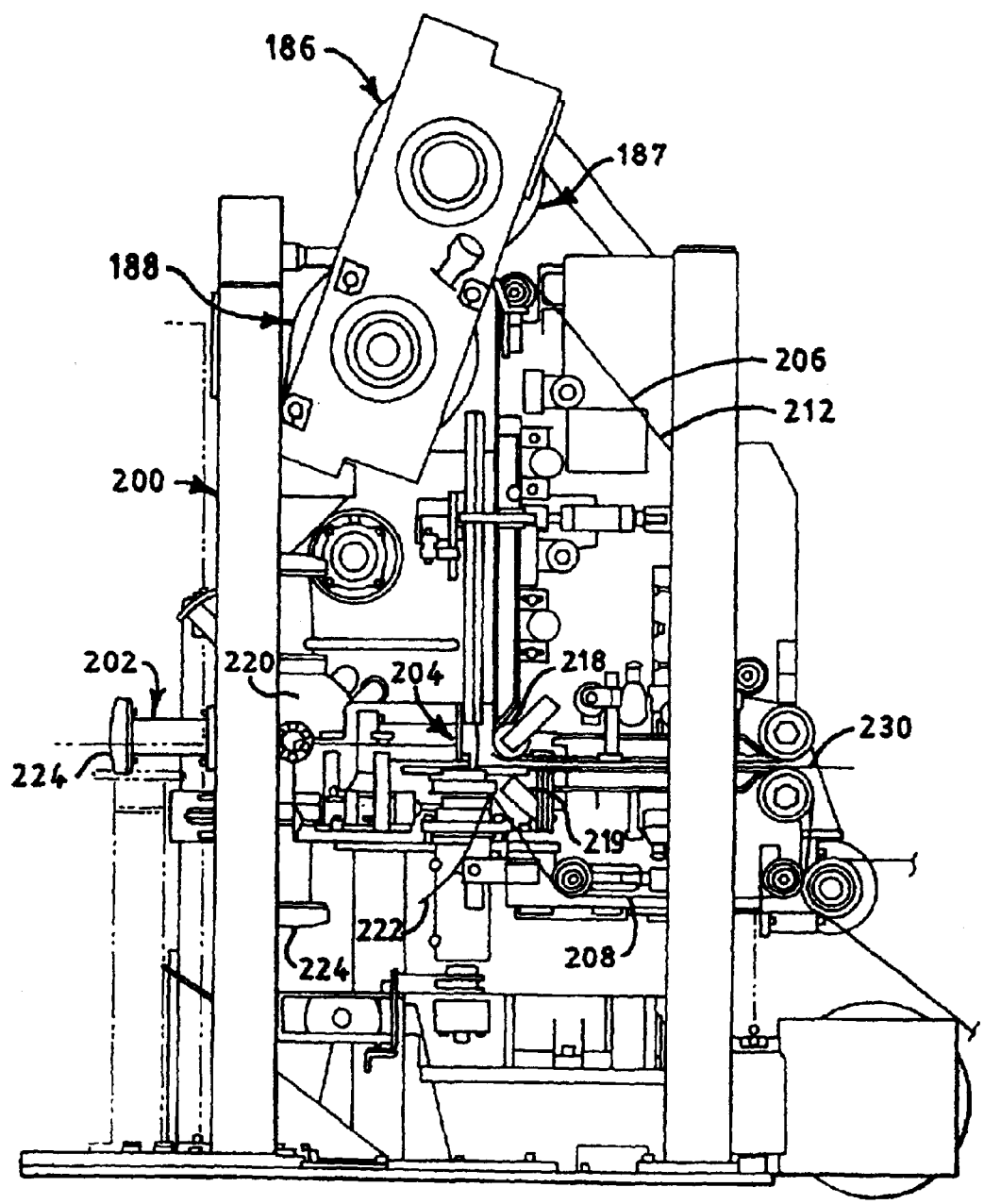
FIG. 2 is a schematic side view of an exemplary embodiment of a folding section for making garments such as training pants, the folding section following the assembly section shown in FIG. 1.
Figure 3:
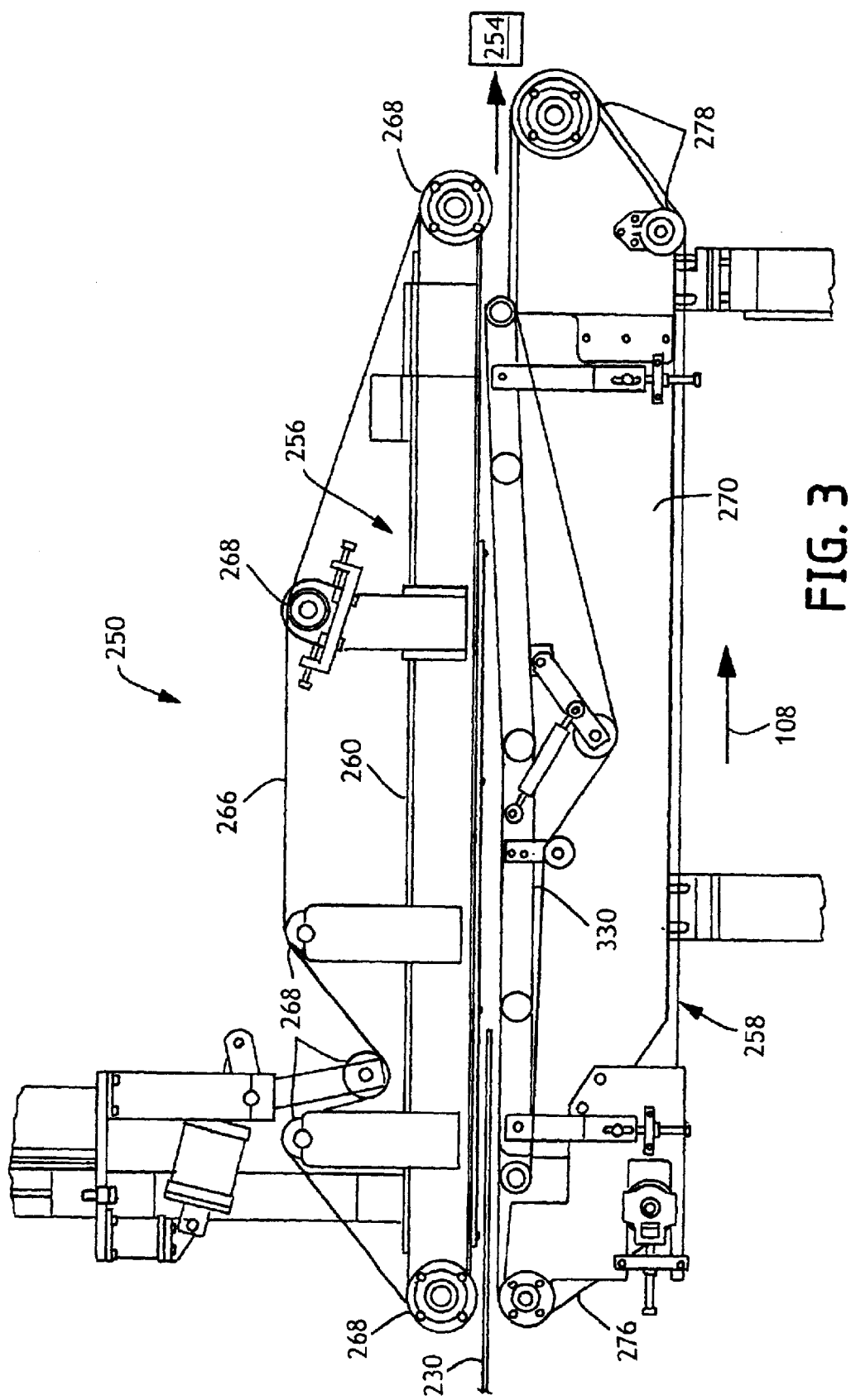
FIG. 3 is a schematic side view of an exemplary embodiment of a seaming section which can follow the folding section shown in FIG. 2.

FIGS. 1–3 representatively illustrate one embodiment of a method and apparatus for making a training pant 20. The training pant 20 is illustrated separately and in a partially fastened condition in FIG. 4. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
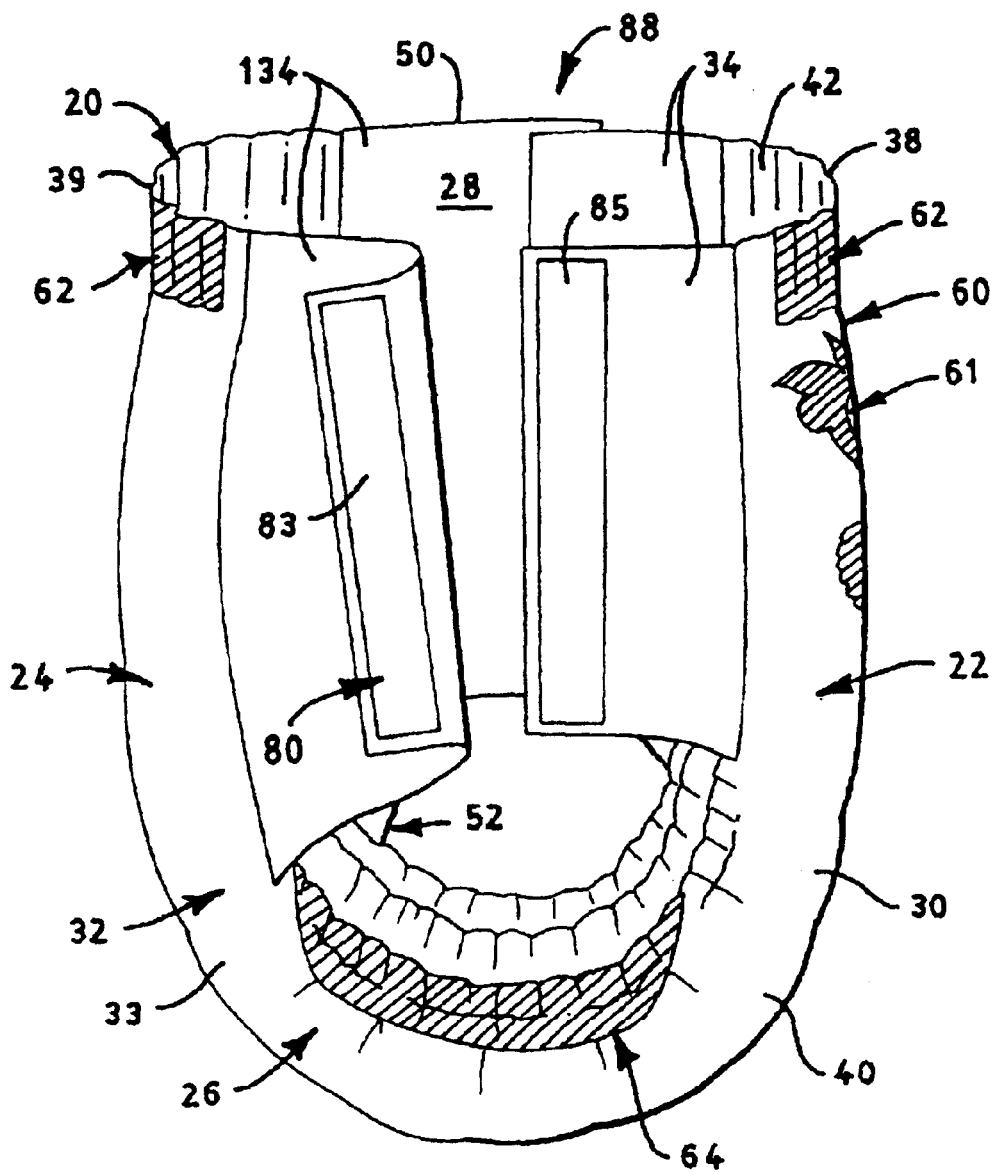
FIG. 4 illustrates a side view of a training pant made by the process and apparatus shown in FIGS. 1–3, where the fastening system is shown engaged on one side of the training pant and disengaged on the other side of the training pant.
Figure 5:
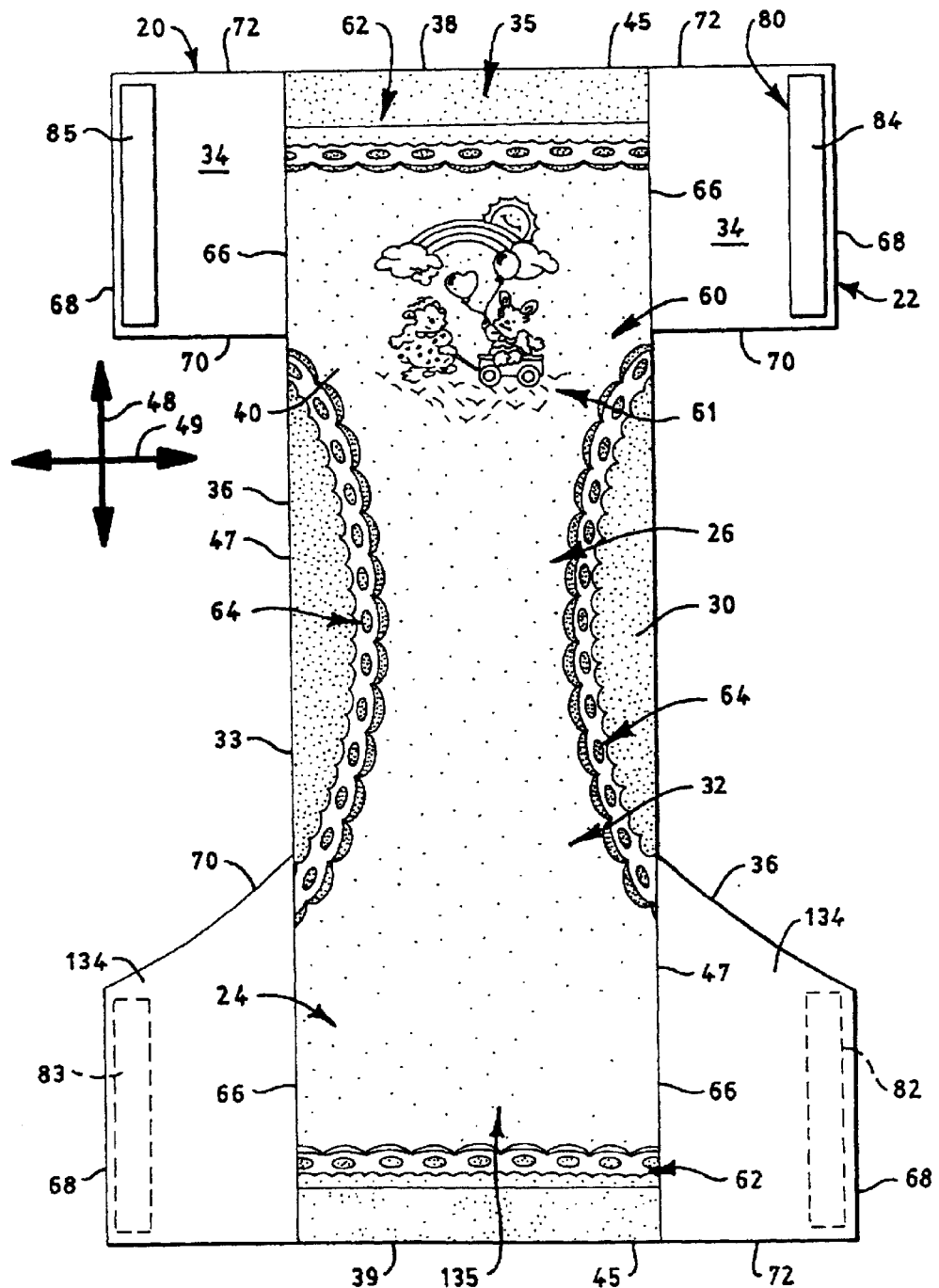
FIG. 5 illustrates a plan view of the training pant shown in FIG. 4 in an unfastened, stretched and laid flat condition, and showing the surface of the training pant that faces away from the wearer.
Figure 6:
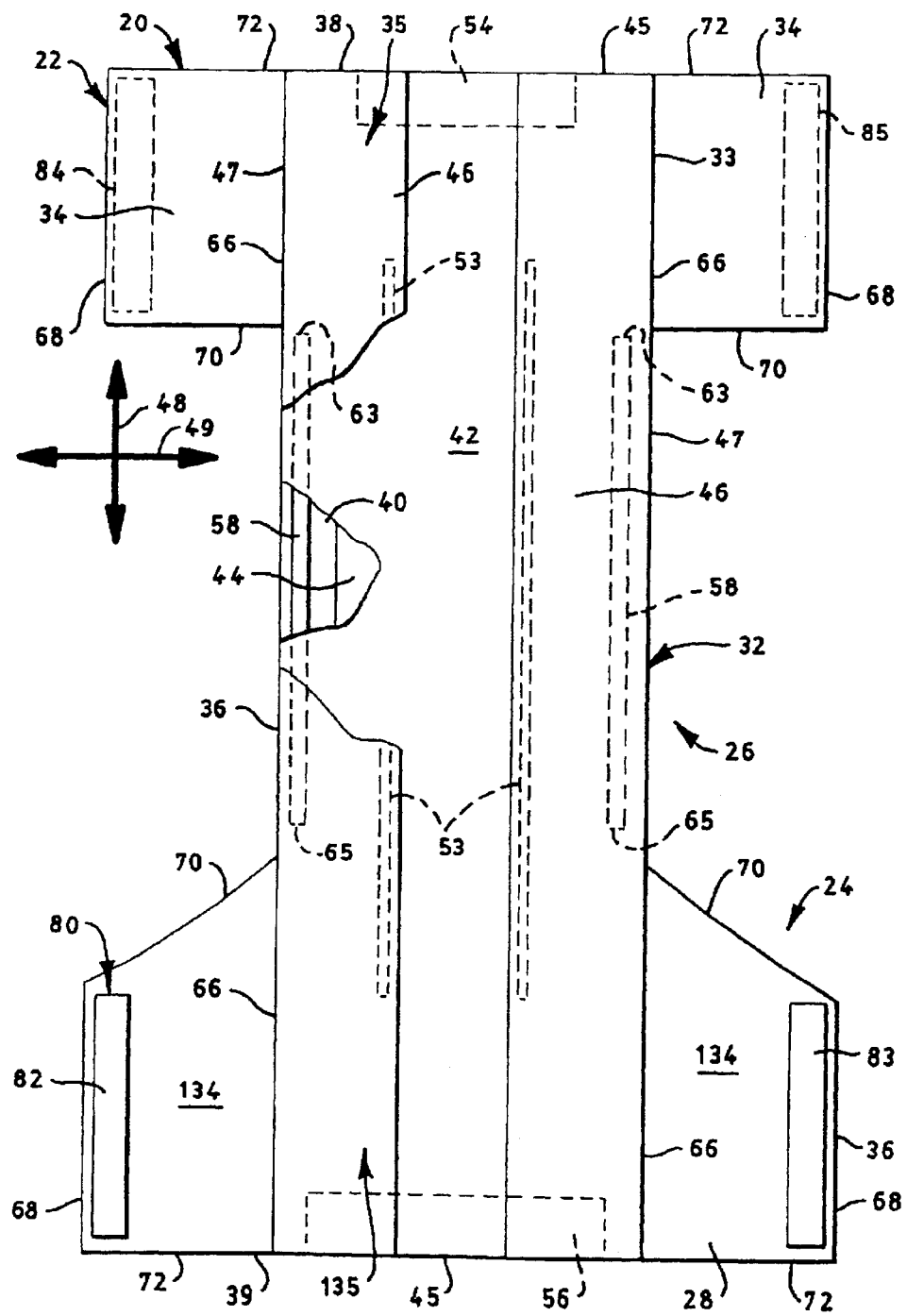
FIG. 6 illustrates a plan view similar to FIG. 5, but showing the surface of the training pant that faces the wearer when the training pant is worn, and with portions cut away to show the underlying features.

The illustrated absorbent chassis 32 comprises a composite structure 33 which can be rectangular or any other desired shape, a pair of transversely opposed front side panels 34, and a pair of transversely opposed back side panels 134. The composite structure 33 and side panels 34 and 134 may comprise two or more separate elements, as shown in FIG. 4, or be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) can be operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a font waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 28 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 4 and 5, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal center line of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a non-woven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can comprise elastomeric materials or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both. commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sept. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 5, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and can be desirably positioned along the distal edges 68 of the front side panels 34, and abutting or adjacent to the waist end edge 72. In certain embodiments, for example, the second fastening components 84 and 85 are located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

The fastening components 82–85 can be adhered to the side panels 34 and 134 by any means known to those skilled in the art such as adhesive bonds, ultrasonic bonds or thermal bonds. The fastening components can comprise separate fastening elements or can comprise distinct regions of an integral material. For example, the training pant 20 can include an integral second fastening material disposed in the front waist region 22 for refastenably connecting to the first fastening components 82 and 83 at two or more different regions, which define the second fastening components 84 and 85 (FIG. 3). In a particular embodiment, the fastening components can comprise integral portions of the waist regions. For instance, one of the elastomeric front or back side panels can function as second fastening components in that they can comprise a material that is releasably engageable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it can be desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is measured parallel to the transverse axis 49 between the longitudinal center lines of the fasteners.

An exemplary embodiment of an assembly section 100 for making a continuous stream of partially assembled, discrete garments 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 1 and 2. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference. Also, the outer cover graphics 61 are not shown in FIGS. 1, 2 and 7.

A continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 1 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cuffing assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 are bonded to the strips 118 of side panel material 116. The location of the fastening components on the composite is a function in part of the configuration of the assembly section 100. The illustrated assembly section 100 is configured so that the upwardly facing surface of the product assemblage 113 will become the outer surface 30 of the training pant 20 and the downwardly facing surface will become the inner surface 28. Moreover, the illustrated assembly section 100 is configured to produce partially assembled training pants 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
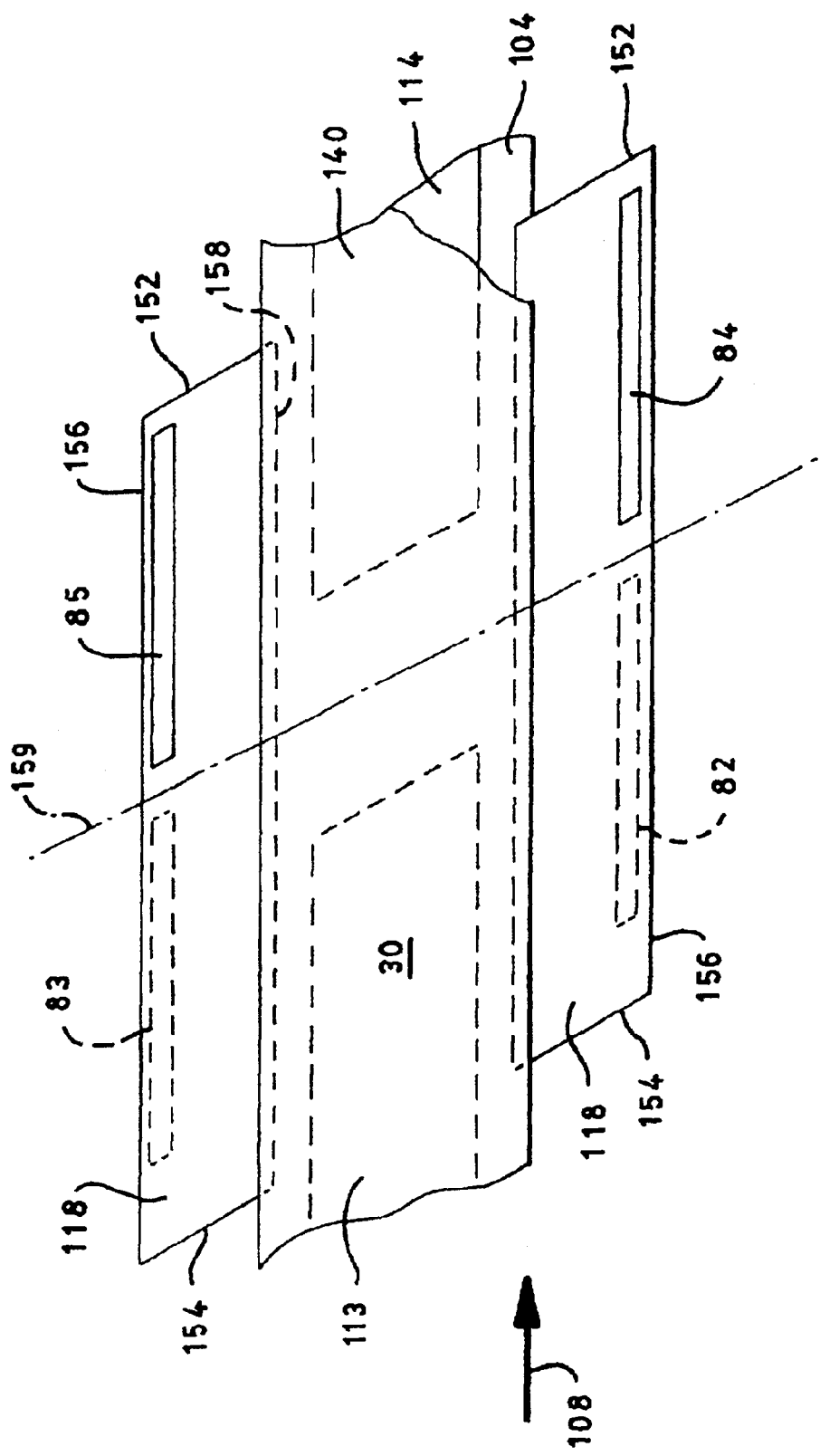
FIG. 7 illustrates a portion of a continuously moving assemblage at one point in the assembly section illustrated in FIG. 1.

The location of the fastening components 82–85 in this embodiment is best illustrated in FIG. 7, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 and 83 can be bonded to the underside of the strips 118 and the second fastening components 84 and 85 can be bonded to the top of the strips. Additionally, the first fastening components 82 and 83 can be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween.

With reference again to FIG. 1, continuous webs of second fastener material 160 used to form the second fastening components 84 and 85 can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83 can be provided from supply rolls 172 or other suitable sources. The first fastener materials 170 can be cut into individual first fasteners 82 and 83 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location, that is the transverse location, of the fastening components 82, 84 and 83, 85. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. patent application Ser. No. unknown, filed on May 15, 2001 by J. D. Coenen et al. and titled "Methods For Making Garments With Fastening Components," which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis. U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 7), continues through the region where the product assemblage 113 will subsequently be cut (see cut line 159 in FIG. 7), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels (FIG. 2). The anvil roll 188 can include a hardened steel rotating roll while the cutting roll 187 can include one or more flexible hardened steel blades damped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

The discrete training pants 102 can then be folded at a folding station 200 using any suitable folding mechanism 202 (FIG. 2). The training pants 102 can be folded about a fold line generally bisecting the training pants. As such, the waist regions 22 and 24 of each training pant 102 are positioned in facing relationship with the side panels 34 and 134 extending laterally outward relative to the longitudinal axis 48 of the training pant. The fold line extends in a lateral direction through the crotch region 26 of the training pant. Desirably, each discrete training pant 102 is consistently folded about the fold line such that the front and back waist edges 38 and 39 of the training pant align with each other.

Figure 8:
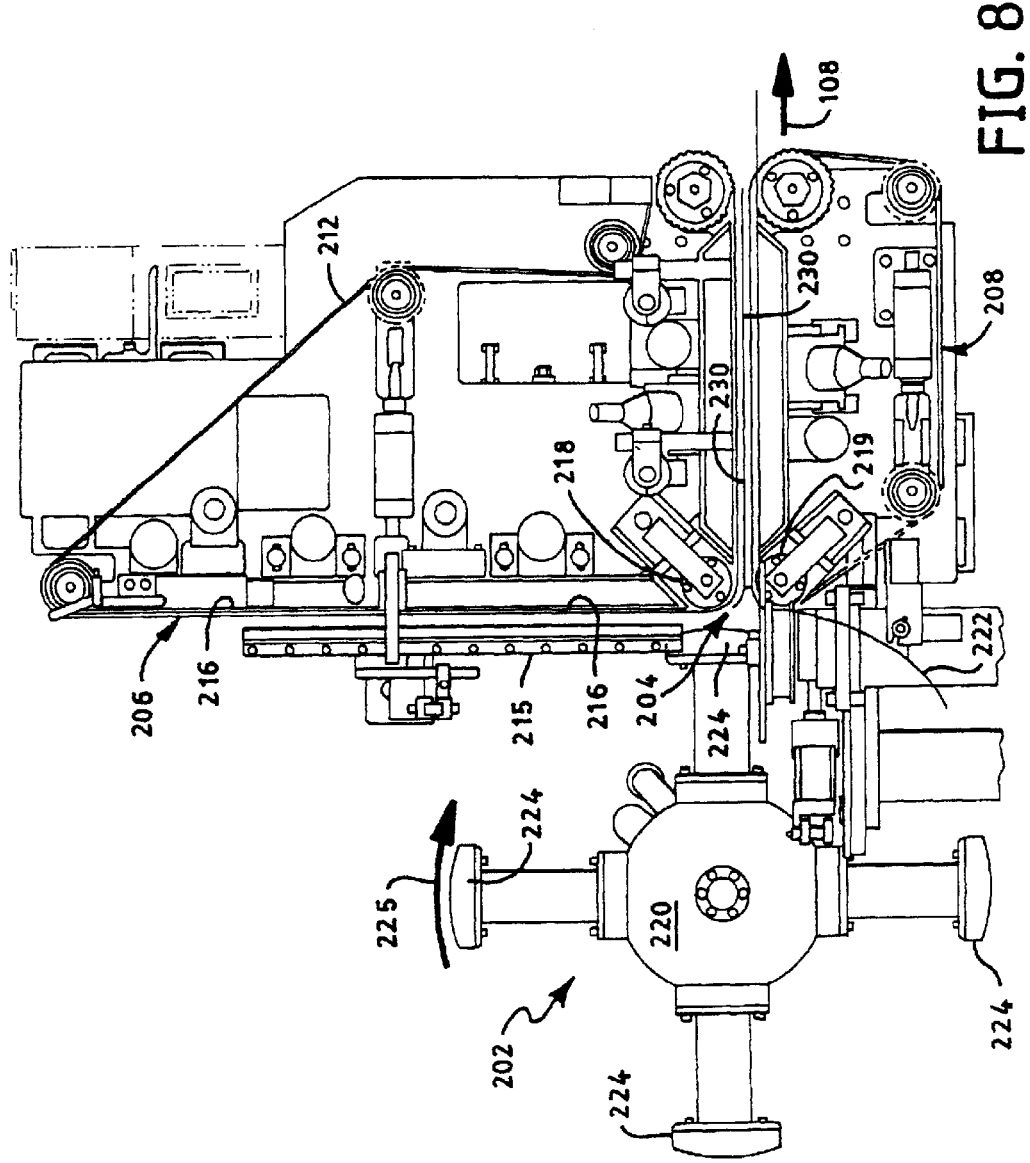
FIG. 8 illustrates an enlarged side view of the folding section shown in FIG. 2.
Figure 9:
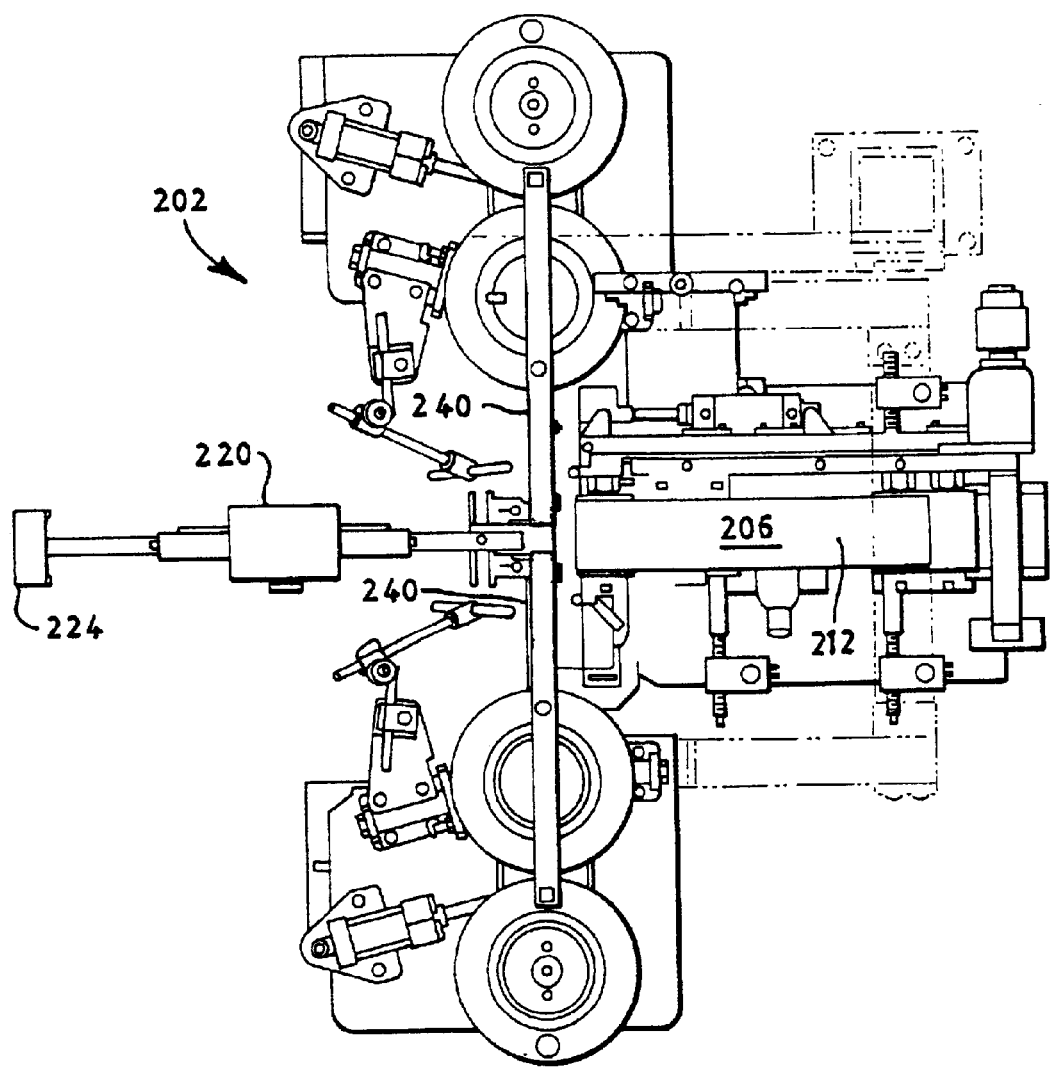
FIG. 9 illustrates a top view of a portion of the folding section shown in FIG. 2.

A variety of folding mechanisms 202 can be used, such as blade folders, linear folders, book folders, tucker blades, or the like. The specific type selected for a given application may depend upon the type of garment being manufactured and the type of fastening mechanism used to secure the garment in a pant configuration. An embodiment of a blade folding mechanism 202 adapted for use with garments incorporating refastenable fastening components 82–85 is illustrated in FIGS. 2, 8 and 9. The illustrated folding mechanism 202 controls the side panels 34 and 134 during folding so that the refastenable fastening components 82–85 are unlikely to engage one another or engage another material during the folding operation. Other arrangements for maintaining separation of the side panels and fastening components during folding are disclosed in U.S. patent application Ser. No. unknown, filed on May 15, 2001 by J. D. Coenen et al. and titled "Folding And Manufacture Of Pants," which is incorporated herein by reference.

The illustrated blade folding mechanism 202 comprises a plurality of rotating folding or tucker blades which are configured to contact the training pant 102 along the fold line. Rotation of the folding blades can force the training pant 102 into a nip 204 between two rotating folding conveyors 206 and 208 causing the training pants to fold about the fold line. The folding conveyors 206 and 208 can form part of a transport system for moving the folded training pants 102 in the machine direction 108. The folded training pants 102 are illustrated as being transported in the machine direction 108 with the crotch region 26 leading the waist regions 22 and 24. Alternatively, the process and apparatus could be modified so that the waist regions lead the crotch region (not shown).

With reference to FIGS. 2, 8 and 9, the series of unfolded, discrete training pants 102 can be transferred from the vacuum anvil roll 188 of the cutter 186 to the upper folding conveyor 206. The training pants 102 can be held by vacuum on the upper folding conveyor 206 and transported toward the nip 204 formed between the folding conveyors 206 and 208. While being transported toward the nip 204, the side panels 34 and 134 can be smoothed out or straightened if desired by various means including fluid stabilizing devices. For example, air knives 215 (FIG. 8), air bars, air nozzles or the like can be mounted in proximity to the upper folding conveyor to provide a stream of fluid directed toward the side panels to stabilize and/or straighten the side panels. The air knives 215 can blow the side panels 34 and 134 against skid plates 216 positioned transversely outward from the upper folding conveyor belt 212. Alternatively, or in addition thereto, the upper folding conveyor 206 can incorporate fluid stabilizing devices consisting of fluid manifolds operatively connected to a high pressure fluid source to fluidly shake the side panels. The fluid stabilizing devices desirably prevent folding of the side panels 34 and 134 as the training pant 102 moves along the upper folding conveyor 206. Sensing devices can also be employed at this point to detect products that have folded side panels or that are misaligned relative to the machine center line.

The product folding nip 204 can be formed between a timed vacuum nose roll 218 of the upper folding conveyor 206 and a timed vacuum nose roll 219 of the lower folding conveyor 208 (FIGS. 2 and 8). As the leading edge of a pant 102 is introduced onto the upper nose roll 218, compressed air can be introduced inside the nose roll to negate vacuum draw of the nose roll. This allows the leading edge of the pant to pass by the nose roll 218 without getting sucked into the nip 204. Alternatively of course, the vacuum source can be temporarily disconnected (isolated) from the nose roll 218. Any suitable control system can be used to repeatedly activate and deactivate vacuum operation of the nose rolls 218 and 219. In particular embodiments, rotary valves can be employed to cycle vacuum to the nose rolls 218 and 219.

A product control drum 220 can guide the leading half of the training pant 102 onto a transfer plate 222 (FIGS. 2 and 8), which may or may not be curved. The product control drum 220 can comprise a plurality of vacuum pucks 224 which rotate in the direction of arrow 225. The illustrated product control drum 220 includes four vacuum pucks 224 to guide four training pants 102 per revolution. Rotation of the product control drum 220 can be timed so that a vacuum puck 224 grabs the leading half of a training pant 102 and transfers the leading edge onto the transfer plate 222. The absorbent chassis 32 and/or side panels 134 of the leading half can be carried on a vacuum puck 224 past the nose roll 219 of the lower folding conveyor 208. Compressed air can be introduced inside this lower nose roll 219 at this point to negate vacuum draw and permit the entire leading edge and side panels 134 to transfer onto the transfer plate 222. Alternatively of course, the vacuum source can be temporarily disconnected (isolated) from the nose roll 219.

With reference to FIG. 9, the folding mechanism 202 can comprise a pair of opposed tucker blades 240 that move in an orbital manner to pass through the vertical path of the training pant 102. The tucker blades 240 can contact the crotch region 26 of the pant 102 and insert the crotch region into the folding nip 204. As this happens, the leading half of the pant 102 reverses direction over the transfer plate 222 and is pulled into the nip 204. The vacuum puck 224 can cease drawing vacuum at this point to release the leading half. Correspondingly, the trailing half of the pant 102 is pulled around the upper nose roll 218. Thus, both halves of the training pant 102 can change from moton in a generally vertical plane to motion between the folding conveyors 206 and 208 in a generally horizontal plane.

Figure 10:
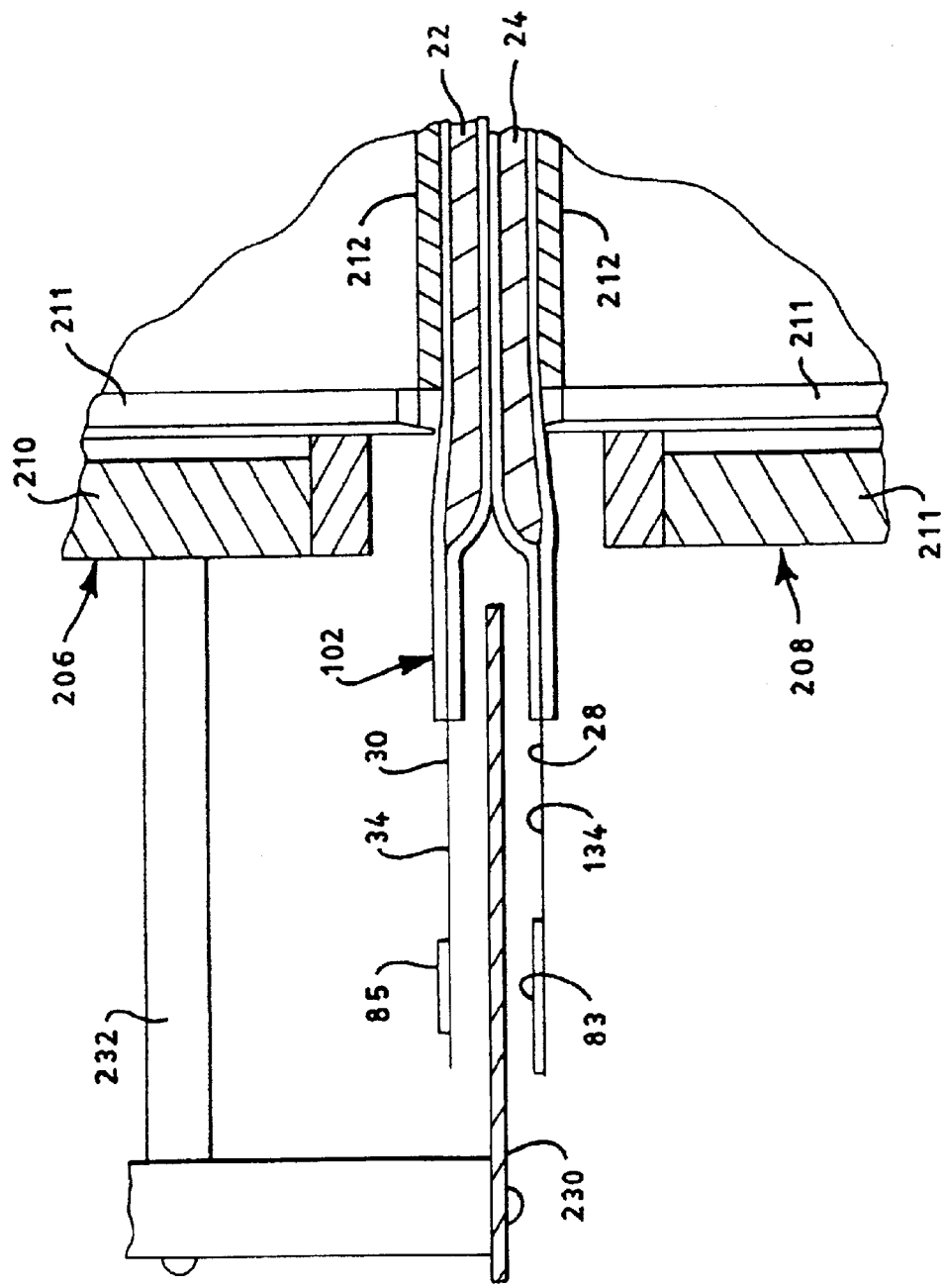
FIG. 10 illustrates an enlarged section view of a portion of a training pant at a position within the folding section shown in FIGS. 2, 8 and 9.

The illustrated folding mechanism 202 can maintain separation between the front and back side panels 34 and 134. As the pant 102 enters the folding nip 204, compressed air can be shut off to the upper nose roll 218 so that the side panels 34 of the trailing half are drawn by vacuum to the upper nose roll. The trailing side panels 34 are thus drawn to the upper nose roll 218 and follow its rotation around the roll and over a side panel separation plates 230 (FIGS. 8 and 10). Similarly, as the leading half of the pant 102 is pulled into the folding nip 204, compressed air can be shut off to the lower nose roll 219 so that the side panels 134 of the leading half are drawn by vacuum to the lower nose roll. The leading side panels 134 are thus drawn to the lower nose roll 219 and follow its rotation around the roll and beneath the side panel separation plates 230.

FIG. 10 illustrates a portion of a partially assembled training pant 102 positioned between the upper and lower folding conveyors 206 and 208 at a location downstream of the nose rolls 218 and 219. At this point, the training pant 102 has been folded in half and is being transported in the machine direction 108 by the conveyors 206 and 208. The illustrated folding mechanism 202 can thus maintain the front side panels 34 separated from the back side panels 134 during folding.

Each folding conveyor 206 and 208 as illustrated in greater detail in FIG. 10 can comprise a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can comprise vacuum conveyors as are well known in the art, in which case the continuous belt 212 can be formed of a fluid permeable material, such as one having holes. The folding conveyors desirably transport the training pants 102 with the longitudinal center line of the training pants traveling on the longitudinal center line of the conveyors. As depicted, the front and back side panels 34 and 134 can project laterally outward from the frame structure 210, outstretched in the cross-machine direction.

While traveling on the folding conveyors 206 and 208, the side panels 34 and 134 can be smoothed out or straightened if desired by various means including fluid stabilizing devices (not shown in FIG. 10). Suitable fluid stabilizing devices can comprise air knives, air bars, air nozzles, vacuum nozzles or the like to provide a stream of fluid directed toward or away from the side panels. The fluid stabilizing devices can be incorporated within either or both of the folding conveyors 206 and 208 or can comprise separate devices positioned in proximity to the conveyors. Other suitable mechanisms for smoothing and straightening the side panels 34 and 134 are disclosed in U.S. Pat. No. 5,046,272 issued Sept. 10, 1991 to Vogt et al., which is incorporated herein by reference. The terms "air" and "fluid" are used interchangeably herein to refer to any gaseous substance, for example, air at ambient temperature. Where the specific application permits, the term "fluid" also includes any liquid medium.

As a result of the illustrated folding mechanism 202, the front waist region 22 and front side panel 34 of the partially assembled training pant 102 are disposed above the back waist region 24 and back side panel 134. The first fastening component 83 is disposed on the inner surface 28 of the back waist region 24 and the second fastening component 85 is disposed on the outer surface 30 of the front waist region 22. In the illustrated embodiment, the transverse linear distance between the first fastening components 82 and 83 is the same as the transverse linear distance between the second fastening components 84 and 85. The orientation and/or type of the side panels and the fastening components can of course be varied from that illustrated.

The separation plates 230 can extend in the machine direction 108 to maintain separation between the front and back side panels 34 and 134. The separation plates 230 can comprise a low friction material or coating, such as: stainless steel; teflon; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like. In particular embodiments, the separation plates 230 can comprise a thin layer of teflon, UHMW-PE, DELRIN or the like glued to a plate formed of steel, aluminum or the like. The separation plates can be mounted using suitable support members 232 (FIG. 10) to either the folding conveyors 206 or 208 or other suitable frame structures (not shown).

From the folding station 200, the continuous stream of discrete, partially assembled and folded training pants 102 enters a seaming section 250, an embodiment of which is shown in FIG. 3. The seaming section 250 can encompass processes and apparatus for controlling the unattached side panels 34 and 134, inverting the fastening components on one pair of side panels, guiding the opposite fastening components into cross-machine direction position with the inverted fastening components, and bonding the fastening components together to form a lap seam. In general, the process and apparatus bend or fold the front or back side panels 34 or 134 approximately 180 degrees using an air flow, solid member, or other suitable device. Additionally, side panel transfer devices 330 can move laterally outward portions of the opposite side panels toward the machine center line so that the fastening components on the opposite side panels are positioned in a corresponding cross-machine direction location as the inverted fastening components. The fastening components can then be brought into contact with one another. In the embodiment shown in FIG. 4, the side panels are refastenably bonded together using mating mechanical fastening components 82–85, although other fastening mechanisms can also be used. The seaming section 250 can thus convert the partially assembled and folded training pants 102 into prefastened training pants 20 each having a waist opening 50 and a pair of leg openings 52 (FIG. 4). The illustrated seaming section 250 could of course be inverted so that the lower side panel forms the inner side panel of the lap seam (not shown). From the seaming section 250, the training pants 20 can be processed through various finishing stations 254, for operations such as side panel tucking, packaging, or the like.

The partially assembled training pants 102 can be transported in the machine direction 108 through the seaming section 250 by a transport system, such as conveyors. In the illustrated embodiment, the training pants 102 are transferred from the upper and lower folding conveyors 206 and 208 (FIGS. 2 and 8–10) to upper and lower alignment conveyors 256 and 258 (FIGS. 3 and 11–18). As illustrated, the upper alignment conveyor 256 can comprise a frame structure 260, one or more vacuum chambers 262 defined within the frame structure, one or more vacuum cover plates 264 mounted on the frame structure and one or more continuous fluid-permeable belts 266 carried on a plurality of rotatable pulleys 268 (FIGS. 3, 11 and 15) or other suitable devices. Similarly, the lower alignment conveyor 258 can comprise a frame structure 270, a vacuum chamber 272 defined within the frame structure, a vacuum cover plate 274 mounted on the frame structure and a continuous fluid-permeable belt 276 carried on a plurality of rotatable pulleys 278 (FIGS. 3, 11 and 15) or other suitable devices. The vacuum cover plates 264 and 274 and related equipment can be adjustable if desired to accommodate various product sizes. A drive system and conveyor shaft (not shown) can be used to rotatively drive one or more of the pulleys 268 and 278. The vacuum chambers 262 and 272 can be operatively connected to a source of vacuum (not shown) and the vacuum cover plates 264 and 274 can be provided with a plurality of holes 269 and 279, respectively. Suitable conveyor mechanisms such as vacuum conveyors or non-vacuum conveyors are available from various commercial vendors. The transport system can comprise any means to convey the folded products.

Figure 11:
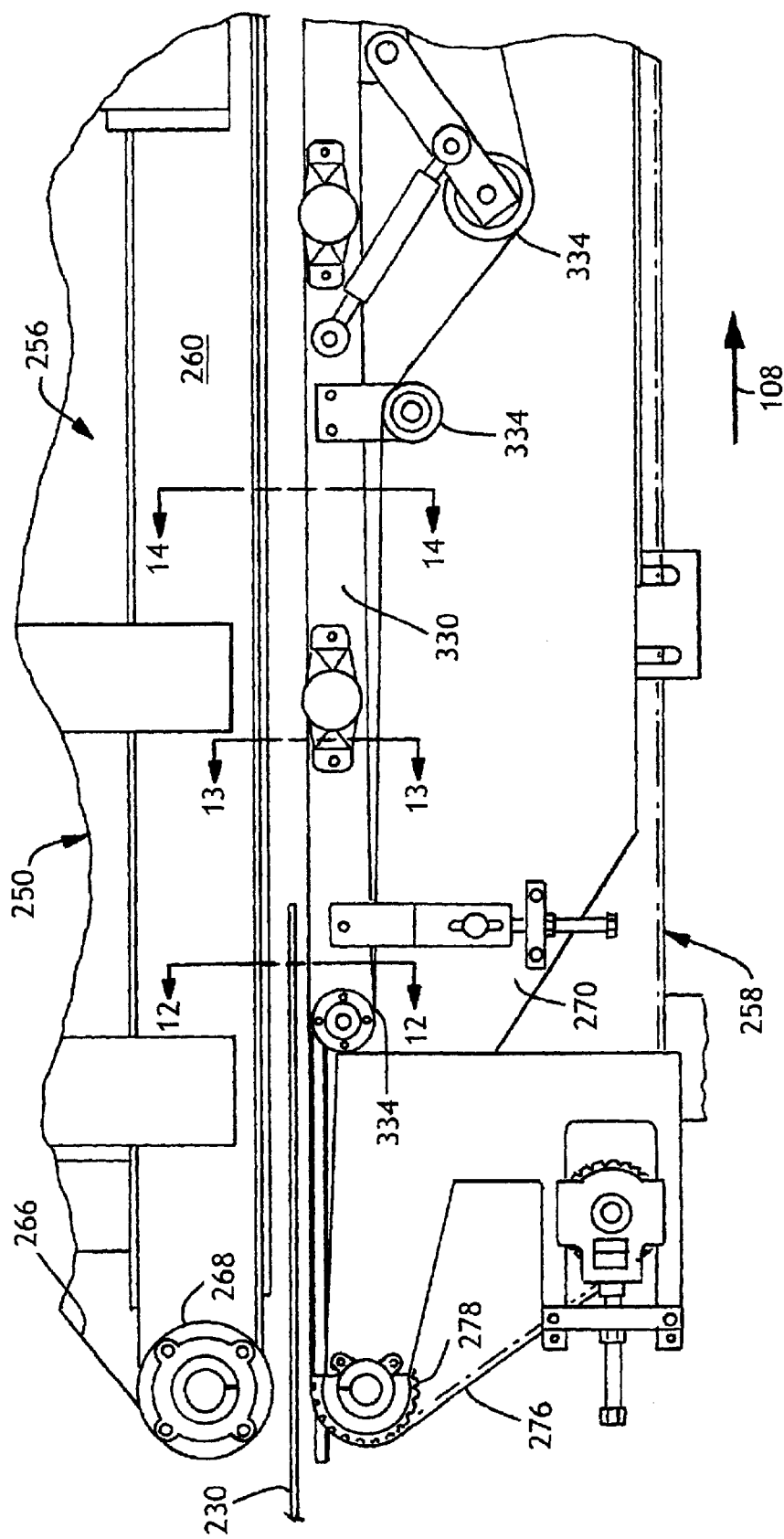
FIG. 11 illustrates an enlarged side view of a portion of the seaming section shown in FIG. 3.

Formation of the side panel lap seam will be described in greater detail with reference to FIGS. 11–20. FIGS. 11 and 15 show enlarged side views of portions of the seaming section 250. FIGS. 12–14 and 16–18 illustrate section views of a portion of a training pant 102 positioned within the seaming section 250 at a series of continually advancing positions. In the illustrated embodiment, the front side panels 34 carrying the second fastening components 84 and 85 (85 shown) form the interior side panel of the lap seam, and the back side panels 134 carrying the first fastening components 82 and 83 (83 shown) form the exterior side panel of the lap seam. The description will focus on the formation of a lap seam and bonding the side panels 34 and 134 together on one side of the training pant 102, although it should be recognized that a lap seam can be formed on the other side of the training pant in a similar manner. The refastenable seams 88 can be formed simultaneously or sequentially on the right and left sides of the pant 102.

For purposes of the present invention, the first fastening components 82 and 83 will be referred to as the initially inward-facing fasteners 82 and 83 because they are positioned between the corresponding left or right side panels when the product is folded in half but prior to formation of the lap seam, and the second fastening components 84 and 85 will also be referred to herein as the initially outward-facing fasteners 84 and 85 because they are on a surface of a side panel that faces away from the other side panel when the product is folded in half but prior to formation of the lap seam. In an alternative embodiment, the training pant 102 could be processed through the seaming section 250 in an inside-out arrangement, in which case the first fastening components 82 and 83 would be considered the initially outward-facing fasteners and the second fastening components 84 and 85 would be considered the initially inward-facing fasteners (not shown).

Figure 12:
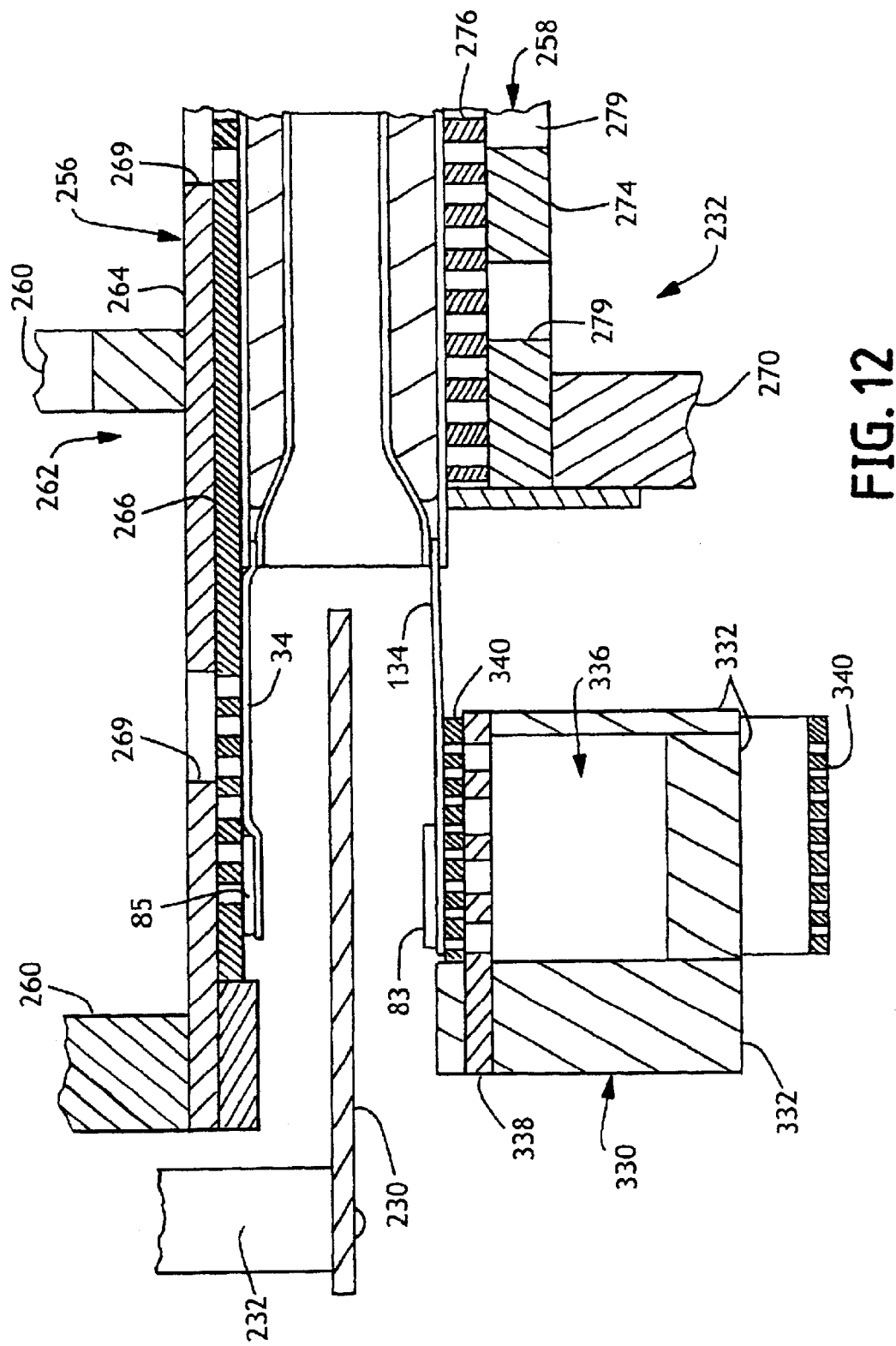
FIG. 12 illustrates an enlarged section view of a portion of a training pant within the seaming section, at the position represented by line 12—12 in FIG. 11.

FIG. 12 illustrates the training pant 102, positioned between the upper and lower alignment conveyors 256 and 258 at a location downstream of the location illustrated in FIG. 10. As shown in FIG. 12, the initially outward-facing fasteners 84 and 85 face the upper alignment conveyor 256. The upper alignment conveyor 256, as illustrated, can have an operative width that is narrower than the full product width. More specifically, the outermost holes 269 of the upper vacuum cover plate 264 can be positioned at locations which corresponds in the cross machine direction with portions of the side panels 34 that are slightly inward from the initially outward-facing fasteners 84 and 85. Alternatively, at least at the machine direction location depicted in FIGS. 12 and 13, the upper alignment conveyor 256 could comprise a full width vacuum conveyor, wherein the full width of the waist region of the training pant 102 can be held by vacuum against the upper conveyor belt 266. The upper alignment conveyor 256 can operate over a range of vacuum, for example, a vacuum of about 2 inches of water or greater below atmospheric pressure.

The lower alignment conveyor 258 can be relatively narrow compared to the upper alignment conveyor 256 and can have a width, for example, equal to the width of the absorbent chassis 32, which permits the back side panels 134 to extend laterally beyond the lower alignment conveyor. In one particular embodiment, the width of the lower alignment conveyor 258 generally corresponds to the distance between the seams 66 (FIGS. 5–6) which bond the side panels 34 and 134 to the absorbent chassis 32. The level of vacuum is preferably sufficient to maintain the waist regions 22 and 24 on their respective alignment conveyors, as the waist regions may not be pinched between the conveyors. Vacuum control of the waist regions will improve positioning and alignment of the side panels 34 and 134. The lower alignment conveyor 258 can operate over a range of vacuum, for example, a vacuum of about 2 to about 8 inches of water or greater below atmospheric pressure.

At the location illustrated in FIG. 12, the back side panels 134 are disposed laterally outward from the lower alignment conveyor 258. The initially inward-facing fasteners 82 and 83 (83 shown) are disposed on the back side panels 134 facing the front side panels 34. The back side panels 134 can be smoothed out or straightened in the seaming section 250 if desired by various means including fluid stabilizing devices. In the illustrated embodiment, the back side panels 134 can be outstretched in the cross machine direction and held in that position by side panel transfer devices 330.

Figure 13:
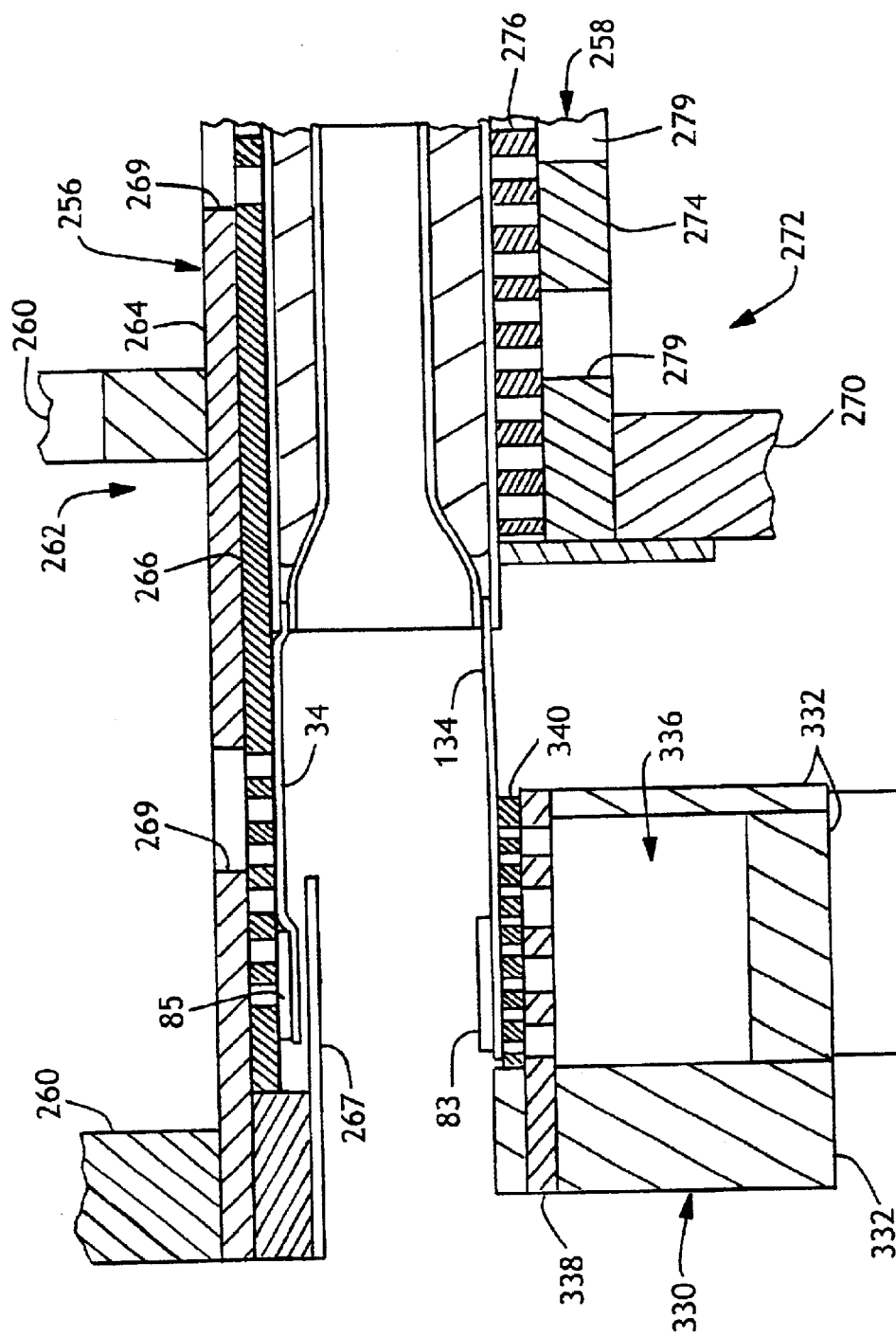
FIG. 13 illustrates an enlarged section view of a portion of a training pant within the seaming section, at the position represented by line 13—13 in FIG. 11.

FIG. 13 illustrates the training pant 102, between the upper and lower alignment conveyors 256 and 258 at a location downstream of the location illustrated in FIG. 12. The back waist region 24 can continue to be transported in the machine direction 108 by the lower alignment conveyor 258 with the back side panels 134 being held and transported in the machine direction by the side panel transfer devices 330. At this point in the seaming section 250, folding guides 267 can be introduced and the conveyors 256 and 258 can be spaced apart a sufficient distance to permit 180 degree inward folding of the initially outward-facing fasteners 84 and 85 (85 shown). The gap between the conveyors 256 and 258 may depend upon the size of the initially outwardly-facing fasteners 84 and 85, and can be, for example, about 2 centimeters. The distance between the alignment conveyors 256 and 258 can be constant or can vary over the machine direction length of the conveyors.

Figure 14:
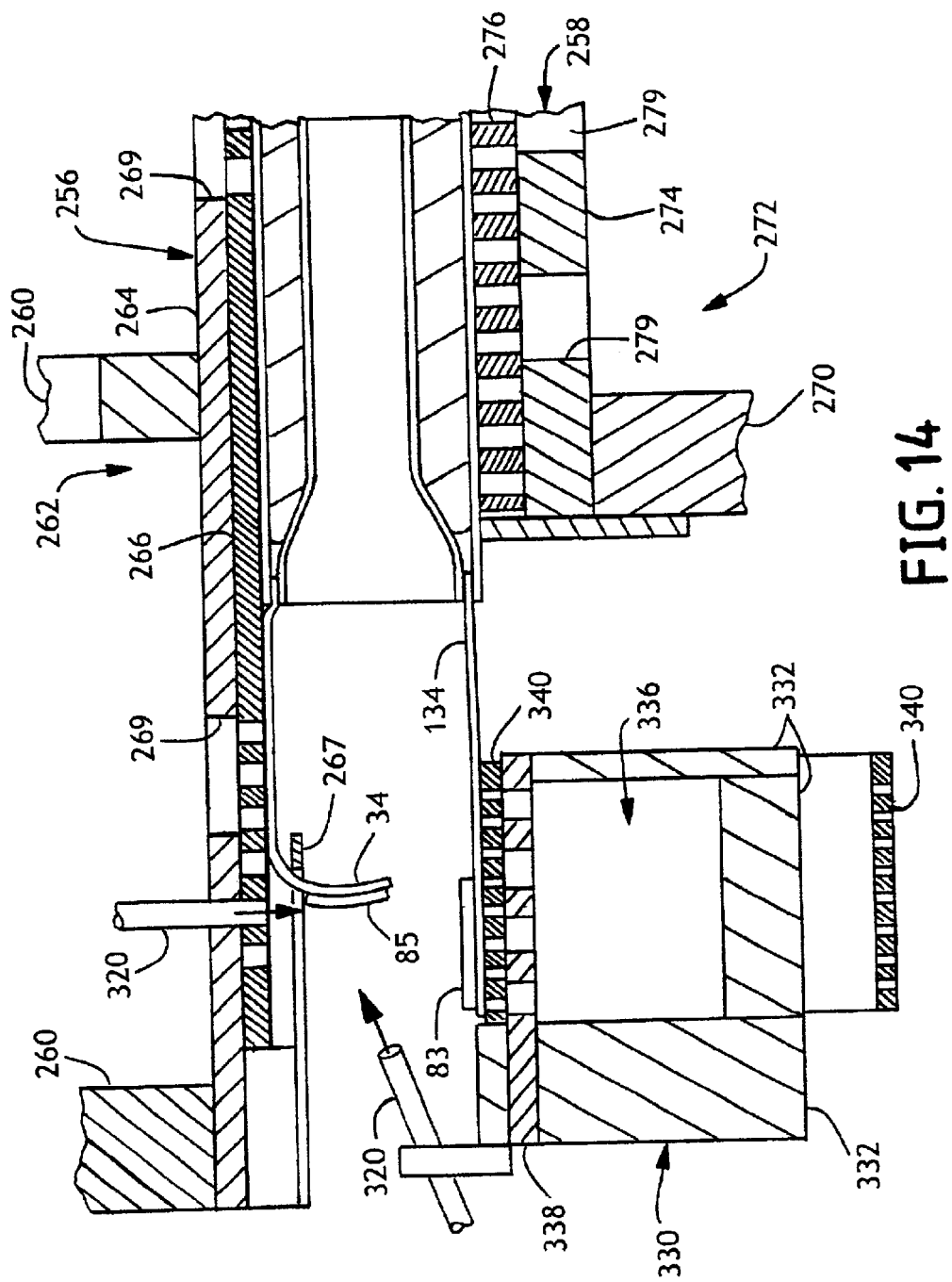
FIG. 14 illustrates an enlarged section view of a portion of a training pant within the seaming section, at the position represented by line 14—14 in FIG. 11.
Figure 15:
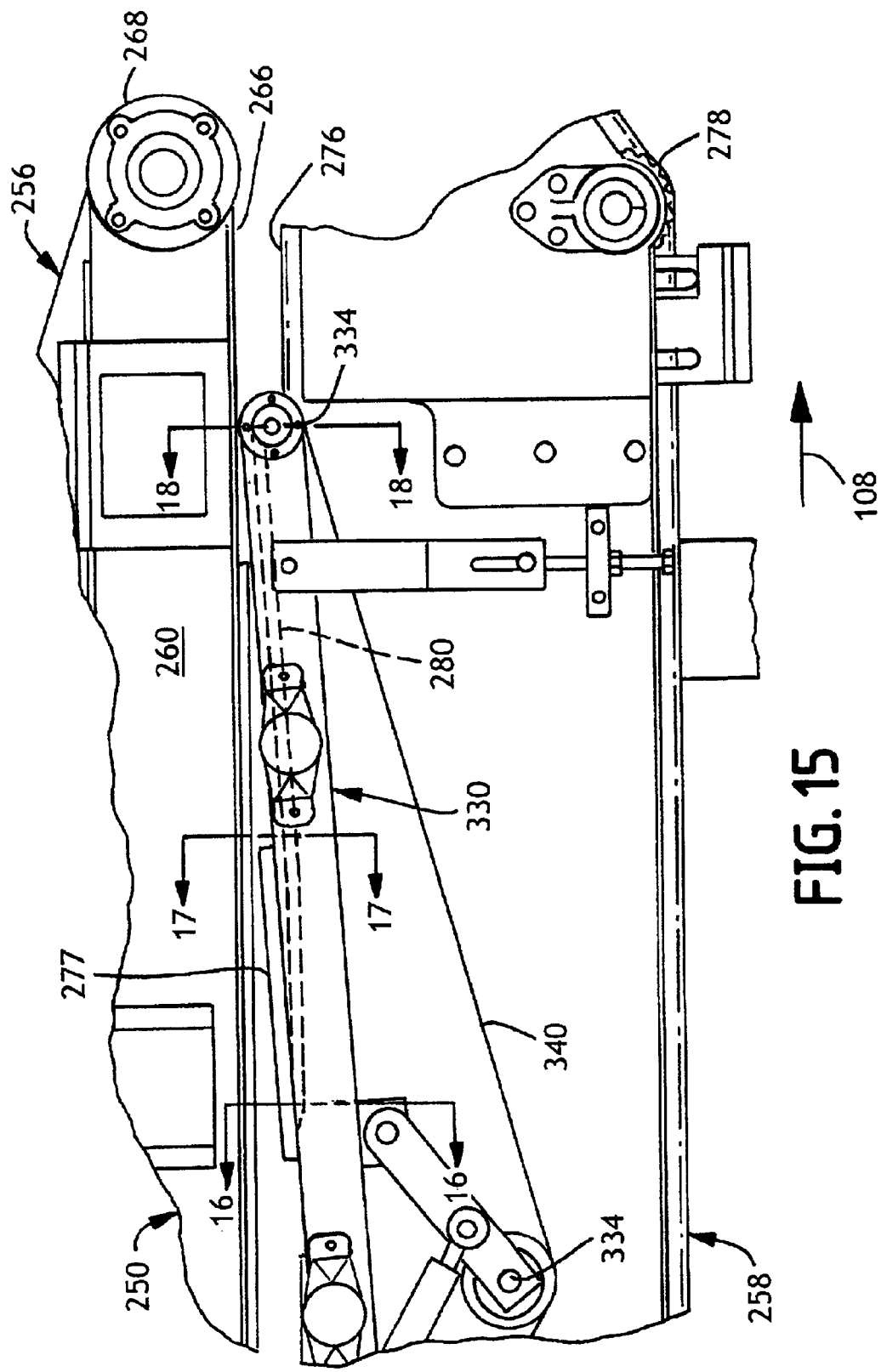
FIG. 15 illustrates another enlarged side view of a portion of the seaming section shown in FIG. 3.

At the machine direction locations illustrated in FIGS. 13 and 14, the upper alignment conveyor 256 can have an operative vacuum width that is less than the full width of the training pant 102 in the front waist region 22, and less than or equal to the distance between the initially outward-facing fasteners 84 and 85. At these locations, the laterally outward portions of the front side panels 34 that include the initially outward-facing fasteners 84 and 85 are not held by vacuum to the upper alignment conveyor. The width of vacuum drawn by the upper alignment conveyor 256 can be modified to accommodate different size products. The width of the upper alignment conveyor 256 can be adjusted by various means, including varying the pattern of holes 269 in the vacuum cover plate 264 or utilizing multiple independent vacuum chambers (not shown).

The upper alignment conveyor 256 can provide a uniform or nonuniform vacuum profile in the cross machine direction. In particular embodiments, the upper alignment conveyor 256 can draw a nonuniform vacuum in the cross-machine direction. Specifically, the upper alignment conveyor 256 can draw a concentrated vacuum at laterally outward regions as well as some area of vacuum in a central region disposed between the laterally outward regions. The laterally outward regions can be positioned such that they correspond to locations of the front side panels 34 immediately laterally inward from the locations of the initially outward-facing fasteners 84 and 85. The concentrated vacuum adjacent the inside edge of the initially outward-facing fasteners 84 and 85 can encourage the inside edge of the fasteners 84 and 85 to function as a hinge point for folding. The concentrated vacuum can be formed by a plurality of slots or an increase in the number of apertures in the vacuum cover plate 264, by separate vacuum chambers, or the like. The focused vacuum in the central region can reduce energy consumption and lessen draw of the back side panels 134 toward the upper alignment conveyor 256.

At the machine direction location illustrated in FIG. 14, each folding guide 267 can narrow to a finger to form a guide for a consistent fold. Thus each folding guide 267 can have a relatively wider portion at the upstream end an a relatively narrower finger extending downstream from the wider portion in a cantilevered configuration. The fingers can act as a hinge point for folding.

In the orientation illustrated in FIG. 14, the laterally outward portions of the front side panel 34, including the initially outward-fadng fasteners 84 and 85, tend to drop from gravity away from the upper alignment conveyor 256. Nonetheless, a mechanical or fluid assist or other panel folding device 320 can be used to inwardly fold the laterally outward portions of the front side panels 34, including the initially outward-facing fasteners 84 and 85, through approximately 180 degrees. Panel folding devices 320 can also be employed in alternative product orientations, for example, where the initially outwardly-facing fasteners are facing downward (not shown) and folding must overcome gravity. In either case, the panel folding devices 320 can assist or can inwardly fold the front side panels 34 onto themselves such that the initially outward-facing fasteners 84 and 85 are facing the opposite side panels 134 and opposite waist region 24. As noted by comparing FIGS. 12 and 16, inward folding of the side panels 34 can cause the initially outward-facing fasteners 84 and 85 (85 shown) to move laterally inward and be positioned closer to the training pant longitudinal center line and the machine center line.

The panel folding device 320 can comprise, for example, one or more air nozzles (FIG. 14) to blow the laterally outward portions of the front side panels 34, including the initially outward-facing fasteners 84 and 85, to a horizontal orientation directed toward the center line of the upper alignment conveyor 256. The panel folding device 320 can operate on a continuous or timed intermittent basis, and can progressively fold the side panels 34 or fold the side panels as a single unit. The panel folding device 320 can alternatively comprise other mechanisms for creating a suitable force to fold or assist to fold the front side panels 34. The panel folding device 320 can alternatively comprise, for example, folding boards or skis which fold the top panel over 180 degrees; a helical surface that pushes the front side panels into the folded configuration; or the like. Once folded inward, the side panels 34 can continue to travel in the machine direction 108 in contact with the folding guides 267. Alternatively, the folding guides 267 can end and the laterally outward portions of the side panels may be drawn toward the upper alignment conveyor 256 by vacuum operating through the folded side panels. In such embodiments, the front side panels 34 will be held by vacuum in a folded configuration.

Use of the terms "vertical" and "horizontal" and variations thereof have their usual meaning, however, the present invention contemplates that vertical surfaces can be "generally vertically" disposed if desired and would thus be oriented between the true vertical position and about a 45 degree position relative to the true vertical position. The same interpretation for "generally horizontally" disposed means an orientation between the true horizontal and about a 45 degree position relative thereto. The terms "upper" and "lower" are provided for ease of understanding, and it should be recognized that the spatial arrangement of the elements being described could be inverted or arranged in another manner.

Figure 16:
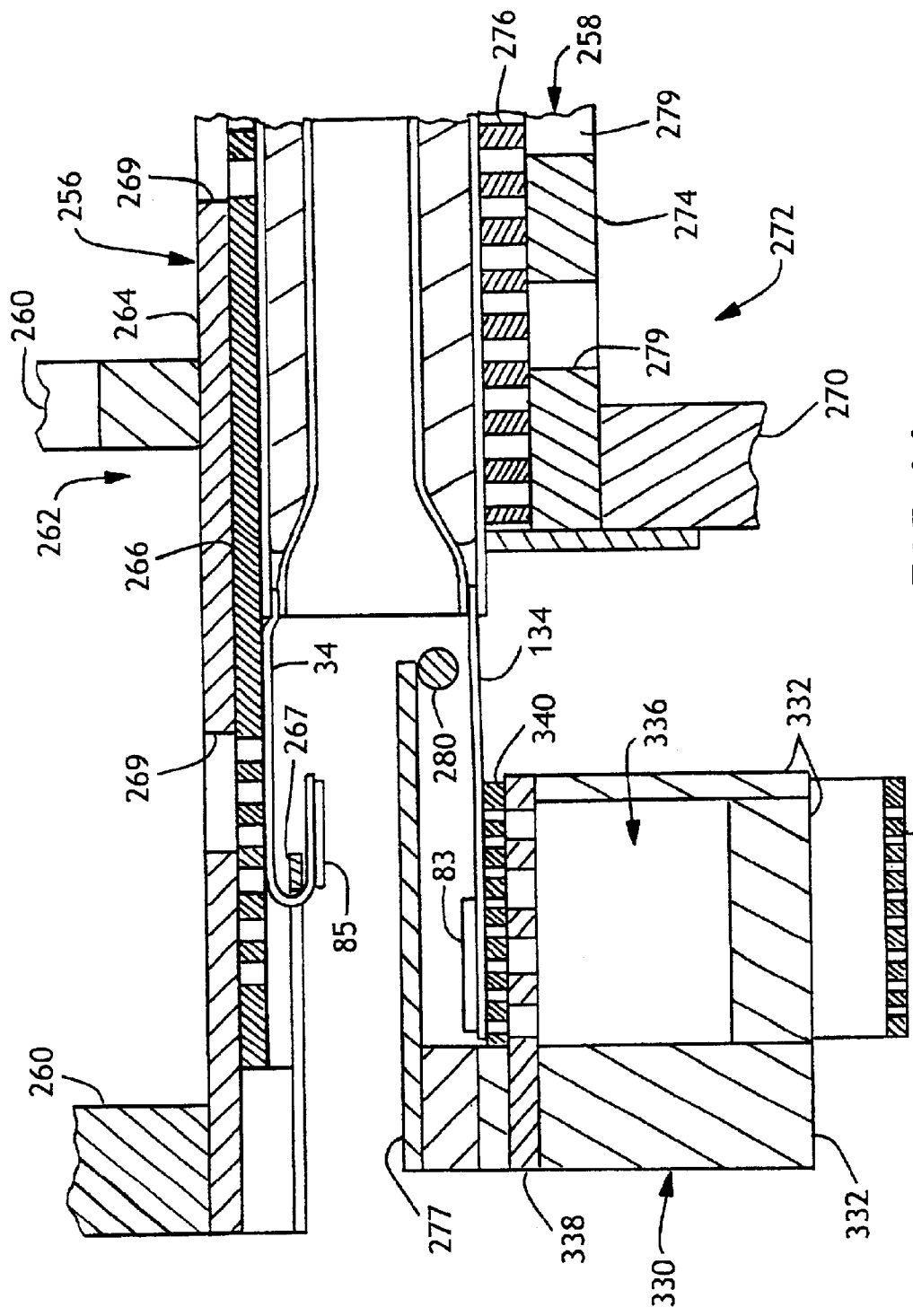
FIG. 16 illustrates an enlarged section view of a portion of a training pant within the seaming section, at the position represented by line 16—16 in FIG. 15.
Figure 17:
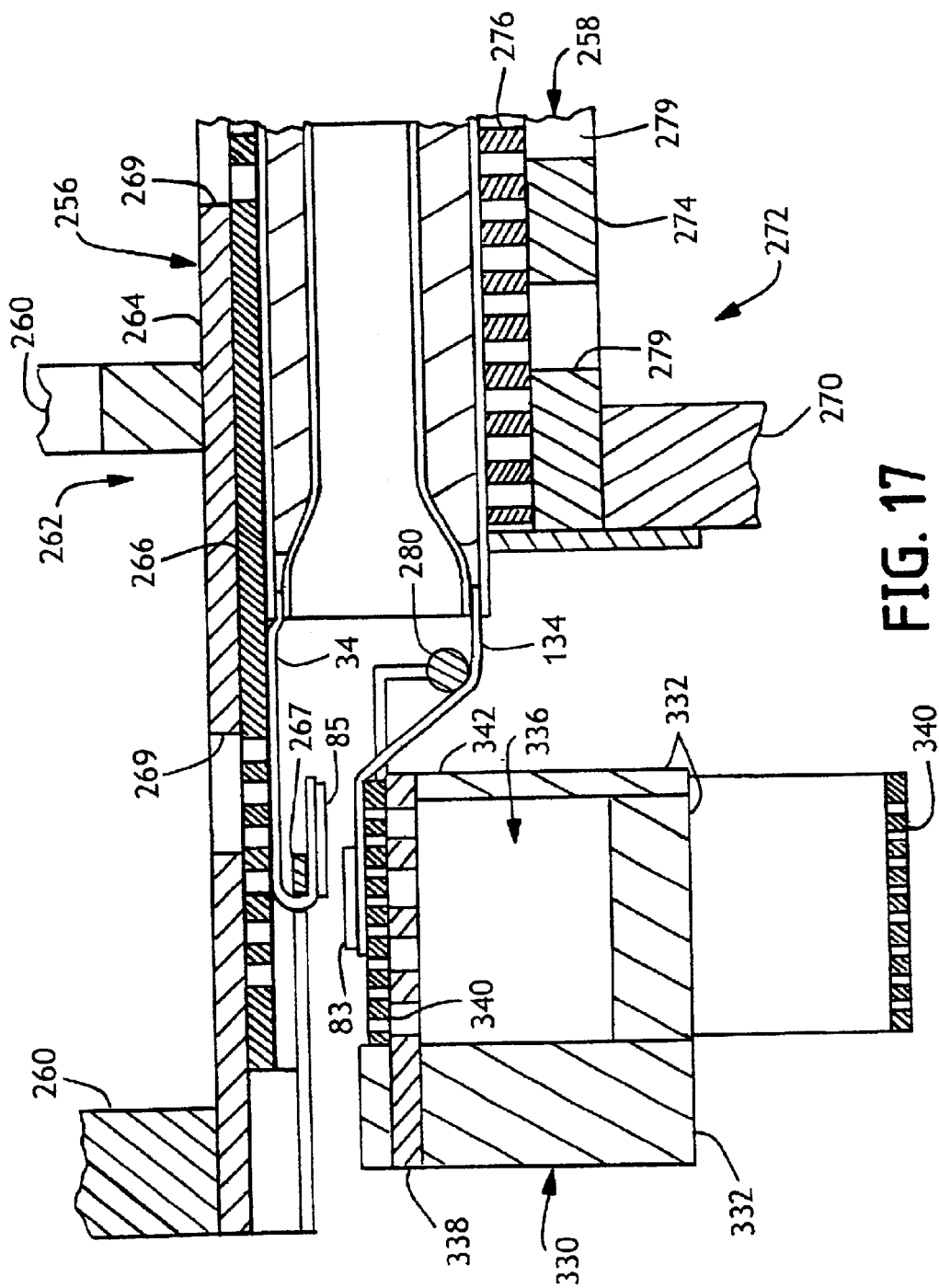
FIG. 17 illustrates an enlarged section view of a portion of a training pant within the seaming section, at the position represented by line 17—17 in FIG. 15.
Figure 18:
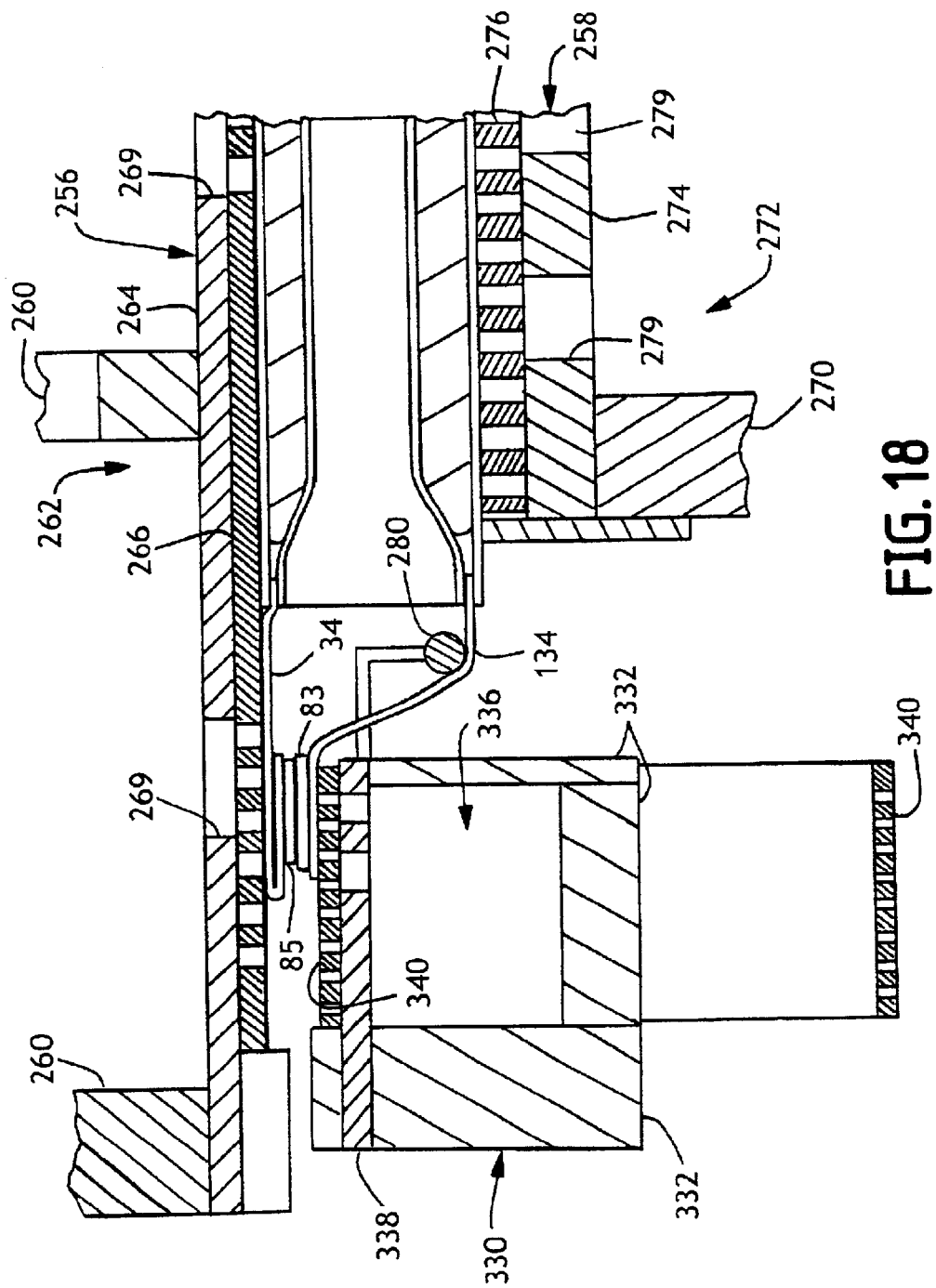
FIG. 18 illustrates an enlarged section view of a portion of a training pant within the seaming section, at the position represented by line 18—18 in FIG. 15.

As the training pants 102 move in the machine direction 108, the back side panels 134 can be transferred to side panel transfer devices 330 (FIGS. 3 and 11–20). As depicted in FIGS. 16–18, the side panel transfer devices 330 can elevate the laterally outer portions of the back side panels 134, including the initially inward-facing fasteners 82 and 83 (83 shown), relative to the lower alignment conveyor 258. More specifically, the alignment conveyors 256 and 258 define therebetween at a specific machine direction location a pant transport plane in which the training pants 102 are carried. The side panel transfer devices 330 carry the side panels on a side panel transport path which is angled with respect to the pant transport plane at such specific machine direction location, so that the pant transport plane and the side panel transport path intersect one another. Consequently, the side panel transfer devices 330 move portions of the back side panels 134 in a "z-direction" perpendicular to the pant transport plane. In doing so, the initially inward-facing fasteners 82 and 83 can move laterally inward toward the center line of the lower alignment conveyor 258 and toward the longitudinal center line of the training pants 102. With further elevation, the side panel transfer devices 330 can also form a nip with the upper alignment conveyor 256 to engage the fastening components 82–85 (see FIG. 18).

As illustrated, the side panel transfer devices 330 can comprise vacuum conveyors which elevate the bottom side panel 134 toward the upper alignment conveyor 256. For purposes of the present invention, the side panel transfer devices 330 are said to be angled toward the pant transport plane at downstream machine direction locations, when the side panel transport path advances closer to the operative surface of at least one alignment conveyor at further downstream positions. The side panel transfer devices 330 can comprise, for example, frame structures 332, a plurality of rotatable pulleys 334 (FIGS. 11 and 15) associated with the frame structures, vacuum chambers 336 defined within the frame structures, vacuum cover plates 338 mounted on the frame structures, and continuous belts 340 carried on the pulleys. A drive mechanism and conveyor shaft (not shown) can be used to rotatively drive one or more of the pulleys 334. The side panel transfer devices 330 can be aligned parallel to the machine direction of the lower alignment conveyor 258 or can be canted inward or outward, for example, to improve side panel alignment with the machine direction.

Figure 19:
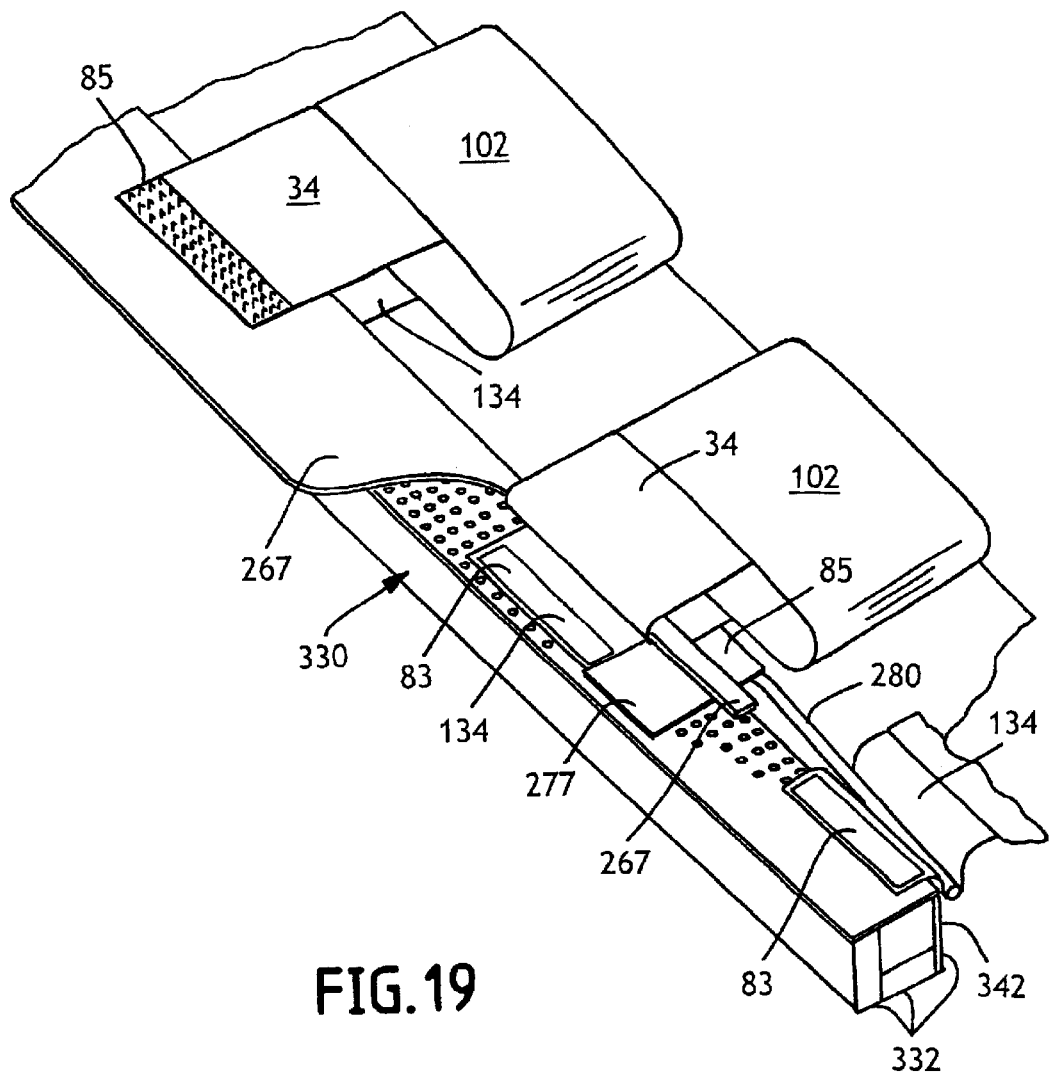
FIG. 19 illustrates an isometric view of a training pant being folded in the seaming section, the view showing folding and tucking guides which can be employed in particular embodiments.
Figure 20:
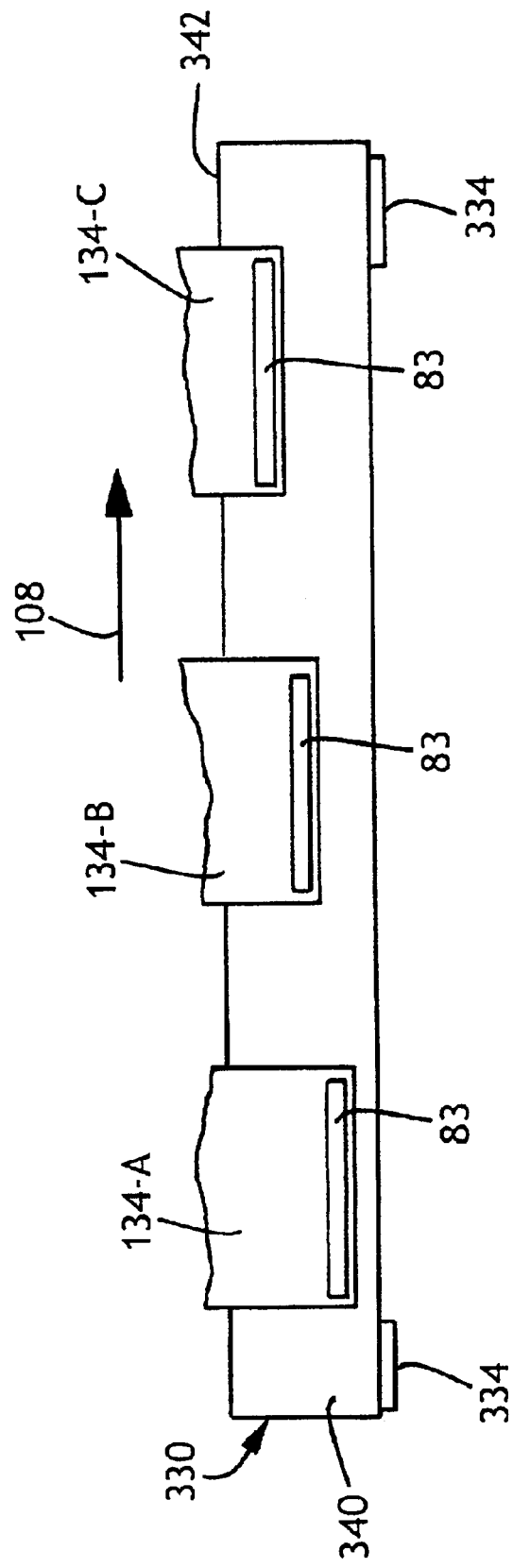
FIG. 20 schematically illustrates a top plan view of a side panel at a sequence of positions on a side panel transfer device shown in FIGS. 3 and 11–19.

FIGS. 19 and 20 isometrically and schematically illustrate a back side panel 134 at a sequence of positions on a side panel transfer device 330. The positions are labeled 134-A, 134-B and 134-C in FIG. 20 in order of advancement in the machine direction 108. With the lower alignment conveyor 258 holding the central portion of the training pant 102 and, in particular the absorbent chassis 32, against the conveyor belt 276 (not shown in FIGS. 19 or 20), the laterally outward portions of the back side panel 134 advance transversely inward as the back side panel 134 is elevated from the plane of the lower alignment conveyor 258 by the upwardly inclined side panel transfer device 330. In effect, the back side panel 134 can be allowed to gradually slip partly off the inward edge 342 of the side panel transfer device 330, desirably to the point where the position of the initially inward-facing fastener 83 is aligned in the cross-machine direction with its corresponding initially outward-facing fastener 85 (see FIG. 18). Because relative movement of the back side panels 134 and the lower alignment conveyor 258 generates transversely inward movement of the initially inwardly-directed fasteners 82 and 83, the back side panels 134 could alternatively be maintained at a constant horizontal position on the side panel transfer devices 330 while the lower alignment conveyor 258 is angled away from the side panel transfer devices.

In particular embodiments, the lower alignment conveyor 258 can maintain the full width of the absorbent chassis 32 in contact with the conveyor belt. Maintaining the full width of the absorbent chassis 32 on the conveyor belt can prevent skewing of the back side panels 134 as they are lifted and can provide maximum inward movement of the fasteners 82 and 83 for a given amount of vertical lift. Tucking guides 277 can be introduced if needed to assist in holding the back side panels 134. Tucking guides 277 can be particularly useful with embodiments where the lower alignment conveyor 258 provides less than full width vacuum. With reference to FIGS. 16, 17 and 19, the illustrated tucking guides 277 are mounted on the side panel transfer devices 330 and define cantilevered arms 280. As best seen by comparing FIGS. 16 and 17, the arms 280 can be mounted at an angle relative to the side panel transport path defined by the side panel transfer devices 330. The arms 280 can be mounted parallel to the pant transport plane, such that the arms can maintain the position of interior portions of the back side panels 134 as the side panel transfer devices 330 lift exterior portions of the back side panels. The arms 280 can extend further downstream, for example to or past the point of engagement of the fastening components (FIG. 18), if desired.

The amount of z-direction movement and cross-machine direction movement of portions of the side panels will depend on several factors, including relative width and positioning of the side panels, the size of the fastening components, the spacing between the side panel transfer devices 330 and the alignment conveyors, the width of vacuum on the alignment conveyors, the location of side panel folding if employed, the use of tucking guides 277, and the like. By way of illustration, the initially inward-facing fastener 83–84 in one embodiment can be elevated approximately 50 millimeters from the plane of the lower alignment conveyor 258 to provide approximately 20 millimeters of inward movement toward the longitudinal center line of the training pant 102.

Again with reference to FIG. 18, toward the downstream end of the side panel transfer devices 330, the initially inward-facing fasteners 82 and 83 (83 shown) can be moved transversely inward to a position which corresponds to the cross-machine position of the initially outward-facing fastener 84 and 85 (85 shown). Additionally, the initially inward-facing fasteners 82 and 83 can be lifted into close proximity and desirably into engagement with the initially outward-facing fasteners 84 and 85. The spacing between the downstream ends of the side panel transfer devices 330 and the upper alignment conveyor 256 can be adjusted to control the level of engagement between the fasteners 82–85. In particular, downstream rolls 334 (FIG. 15) of the side panel transfer devices 330 can be positioned to nip the fasteners together. The illustrated side panel transfer devices 330 can provide progressive inward motion on the full width of the bottom side panels 134 and progressive attachment in the machine direction of the fastening components 82–85.

The side panel transfer devices 330 can be positioned at the same machine direction 108 location in the seaming section 250. Alternatively, the side panel transfer devices 330 can be staggered in the machine direction 108 to allow for cross-machine direction movement-control devices or operations used in combination with a single side panel transfer device. The cross-machine direction movement-control devices or operations can comprise any suitable devices or operations which maintain cross-machine direction control of the training pant 102 during operation of the side panel transfer device.

An alternative embodiment of the method and apparatus for making a training pant 102 are illustrated in FIGS. 21–24. First and second fastening components 400 and 401 are disposed on respective first and second integral side panels 402 and 403. The first fastening component 400 comprises a distal region of the first side panel 402 which is engageable with the second fastening component 401. The second fastening component 401 as illustrated was previously inverted and can be held in place by the upper alignment conveyor 256. As the training pant 102 is transported in the machine direction, the first side panel 402 can be positioned on and can slide over a guide plate 406, which is curved in the machine direction and formed of a suitable low friction material.

Figure 21:
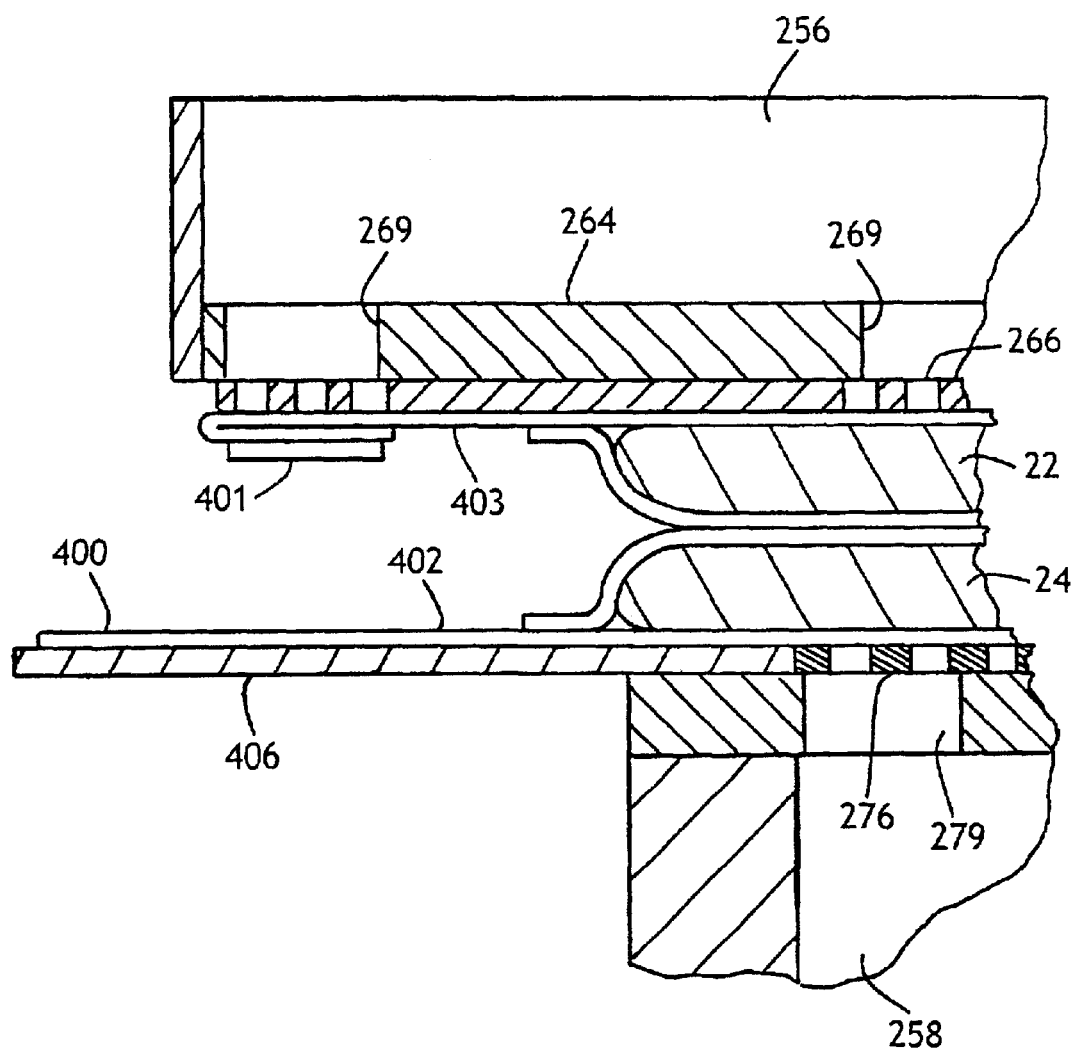
FIGS. 21 through 24 illustrate another embodiment of the method and apparatus for making garments.
Figure 22:
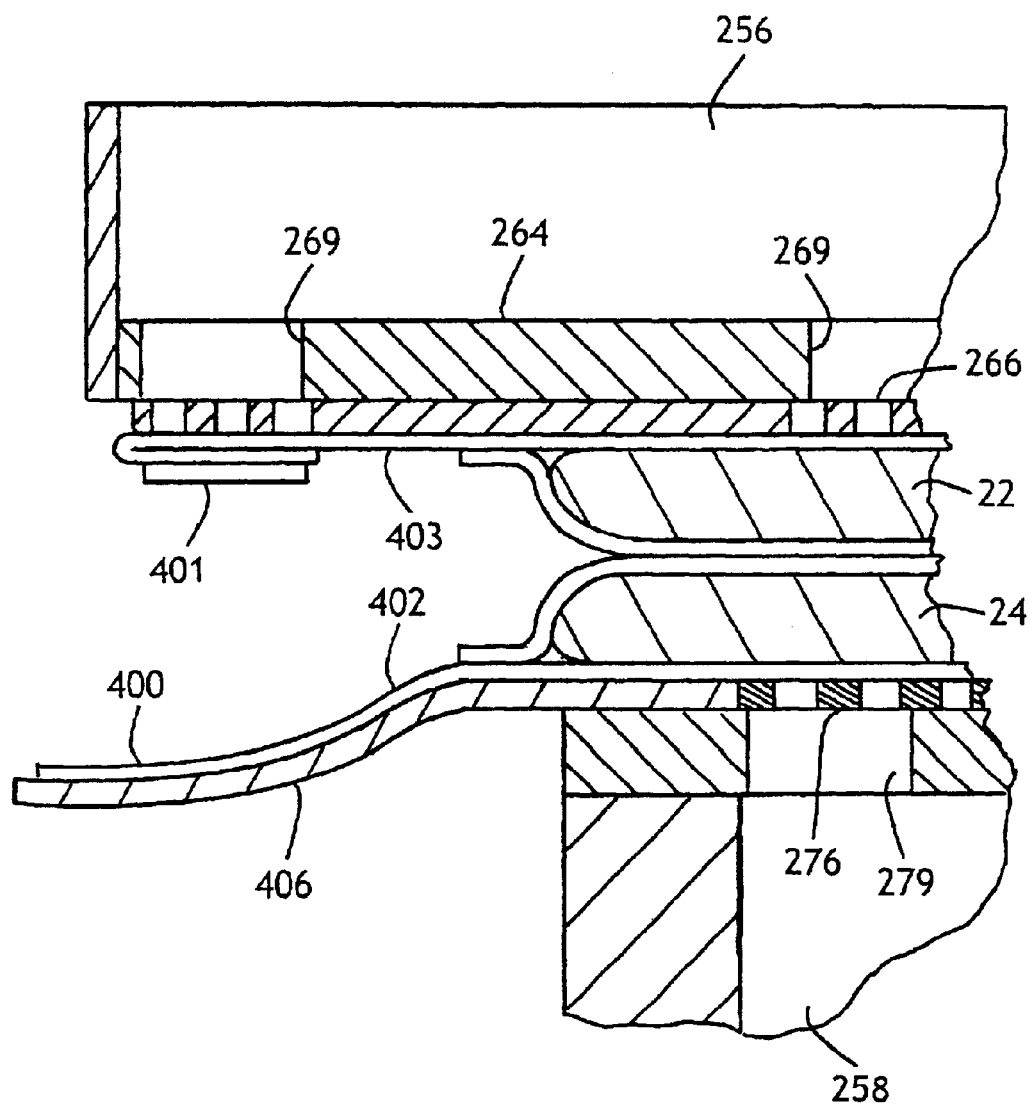

FIG. 22 illustrates the training pant 102 between the upper and lower conveyors 256 and 258 at a location downstream of the location illustrated in FIG. 21. The first side panel 402 is caused to remain in close proximity to or contact with the curved guide plate 406. Tucking guides, air nozzles, or other suitable devices (not shown) can be used to assist in holding the first side panel 402 against the guide plate 406. For example, an air bar (not shown) can be disposed between the conveyors 256 and 258 from the position illustrated in FIG. 21 through the position illustrated in FIG. 23 to direct air toward the first side panel 402.

With the lower alignment conveyor 258 holding the central portion of the training pant 102 against the conveyor belt 276, the laterally outward portions of the first side panel 402 advance transversely inward as the first side panel 400 is shaped on the curved guide plate 406. In particular embodiments, the curvature of the guide plate 406 can be determined so that the first fastening component 400 is inwardly repositioned to the point where the first fastening component is aligned in the cross-machine direction with its corresponding second fastening component 401. The fastening components 400 and 401 are shown aligned in the cross-machine direction in FIG. 23.

Figure 23:
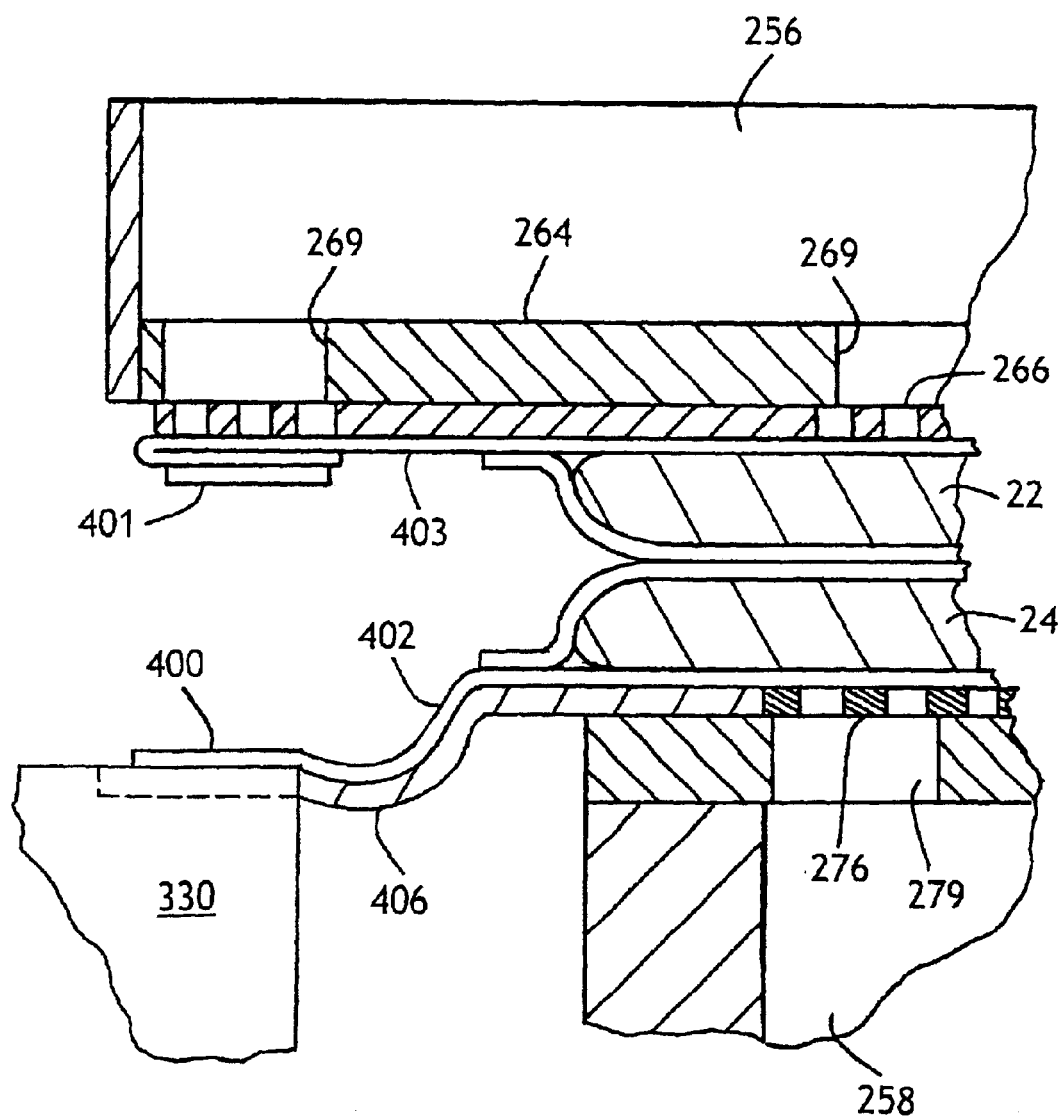
Figure 24:
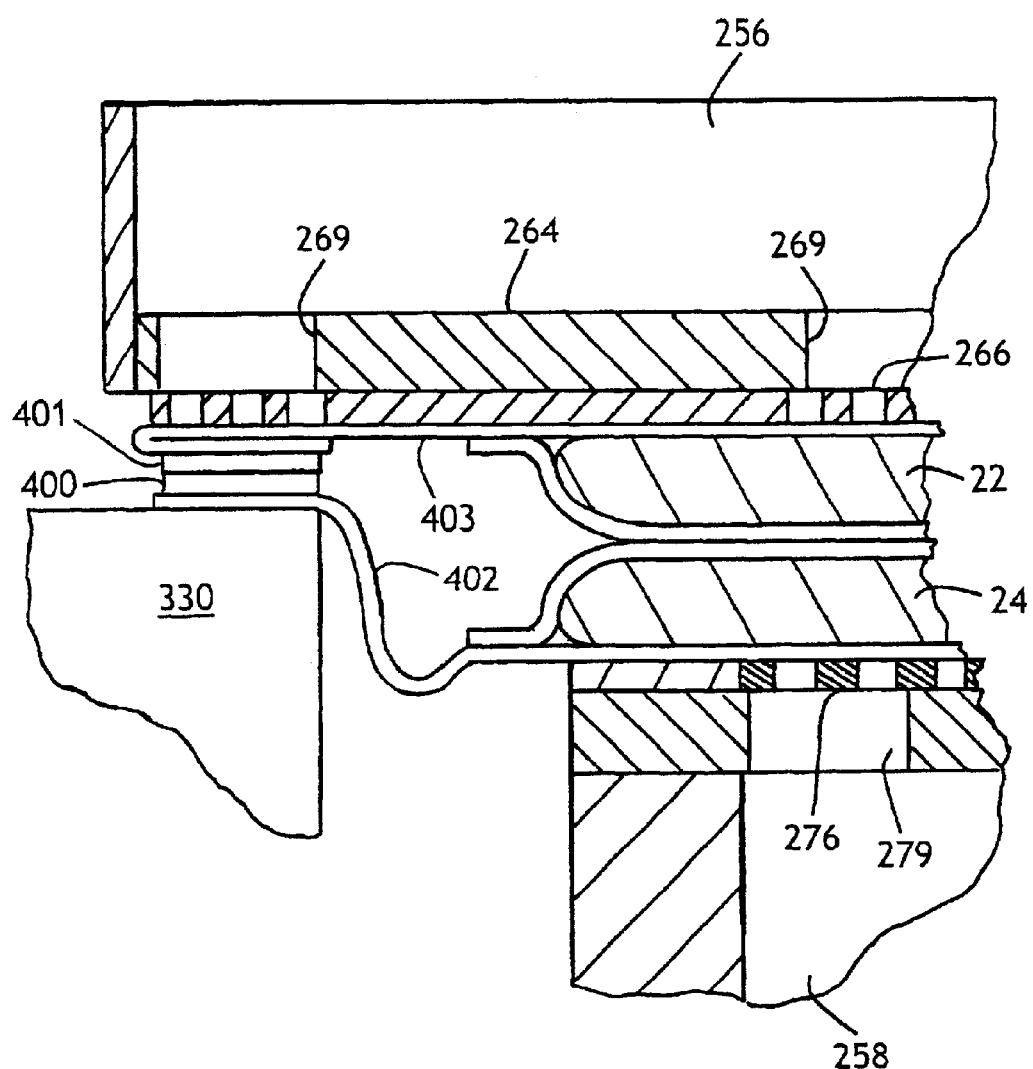

As further depicted in FIG. 23, the first side panel 402 can be transitioned from the curved guide plate 406 onto a side panel transfer device 330. The side panel transfer device 330 can be constructed in the same manner as previously described and thus is not shown in detail. With additional reference to FIG. 24, the side panel transfer device 330 can elevate the laterally outer portions of the first side panel 402 toward the second side panel 403. In particular, the side panel transfer device 330 can define a side panel transport path which is angled with respect to the pant transport plane, so that the first fastening component 400 can be transported in the z-direction into proximity to or engagement with the second fastening component 401. Tucking guides (see FIG. 19) can be disposed between the conveyors and in contact with the first side panel 402 from the position illustrated in FIG. 23 through the position illustrated in FIG. 24. Because the desired cross-machine direction position of the first fastening component 400 had previously been established (FIGS. 21–23), the first side panel 402 can be maintained at a constant cross-machine direction position while the pant 102 is transported in the machine direction and the side panel resides on the side panel transfer device 330.

A further alternative embodiment of the method and apparatus for making a training pant 102 is illustrated in FIGS. 25–29, which depict section views at a series of advancing positions in the machine direction 108. The method and apparatus illustrated in FIGS. 25–29 correspond to that portion of the process described previously in relation to FIGS. 21–24. A pair of side panels can be transferred to fluid flow devices 430 to change the elevation of the laterally outward portions of the side panels relative to the pant transport plane. The laterally outward portions can comprise fastening components, formed by integral engageable regions or by distinct components disposed on the side panels, as illustrated. It should be understood that fluid flow devices 430 are positioned on opposite sides of the machine center line, despite only one side of the machine center line being illustrated.

Figure 25:
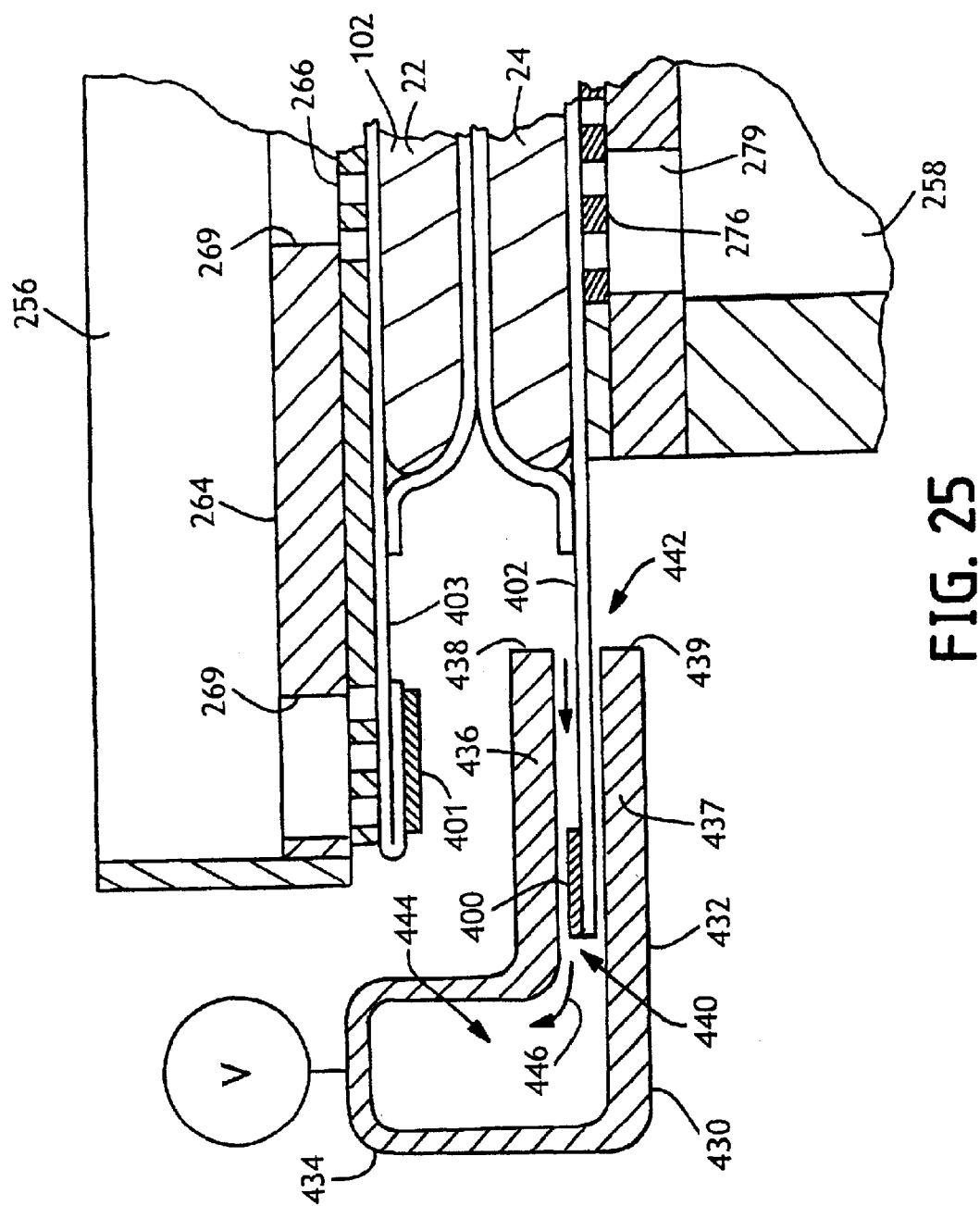
FIGS. 25 through 29 illustrate section views of an embodiment of the present method and apparatus for making garments, and depicting a portion of a training pant positioned at a series of continually advancing positions in the machine direction.
Figure 26:
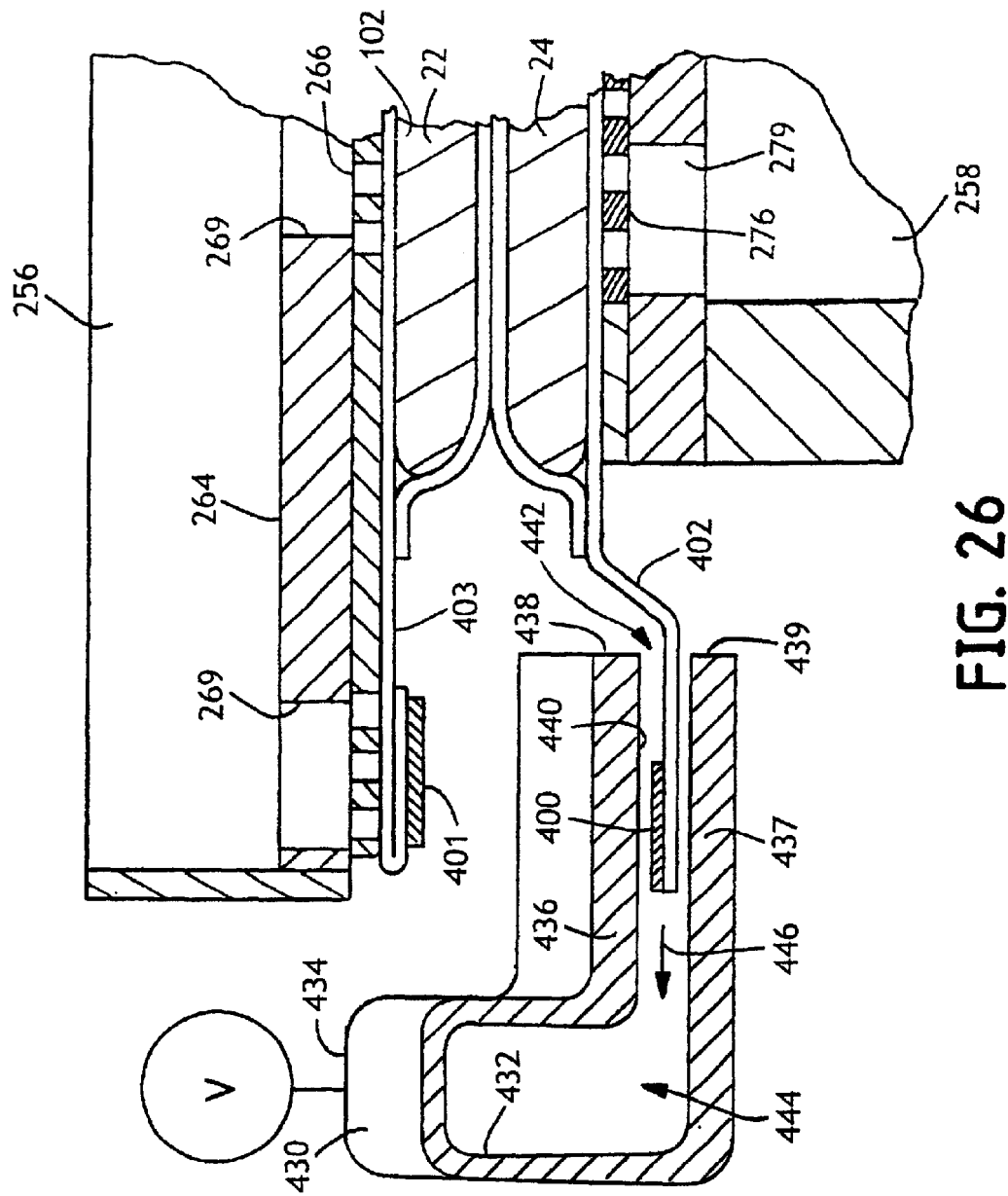
Figure 27:
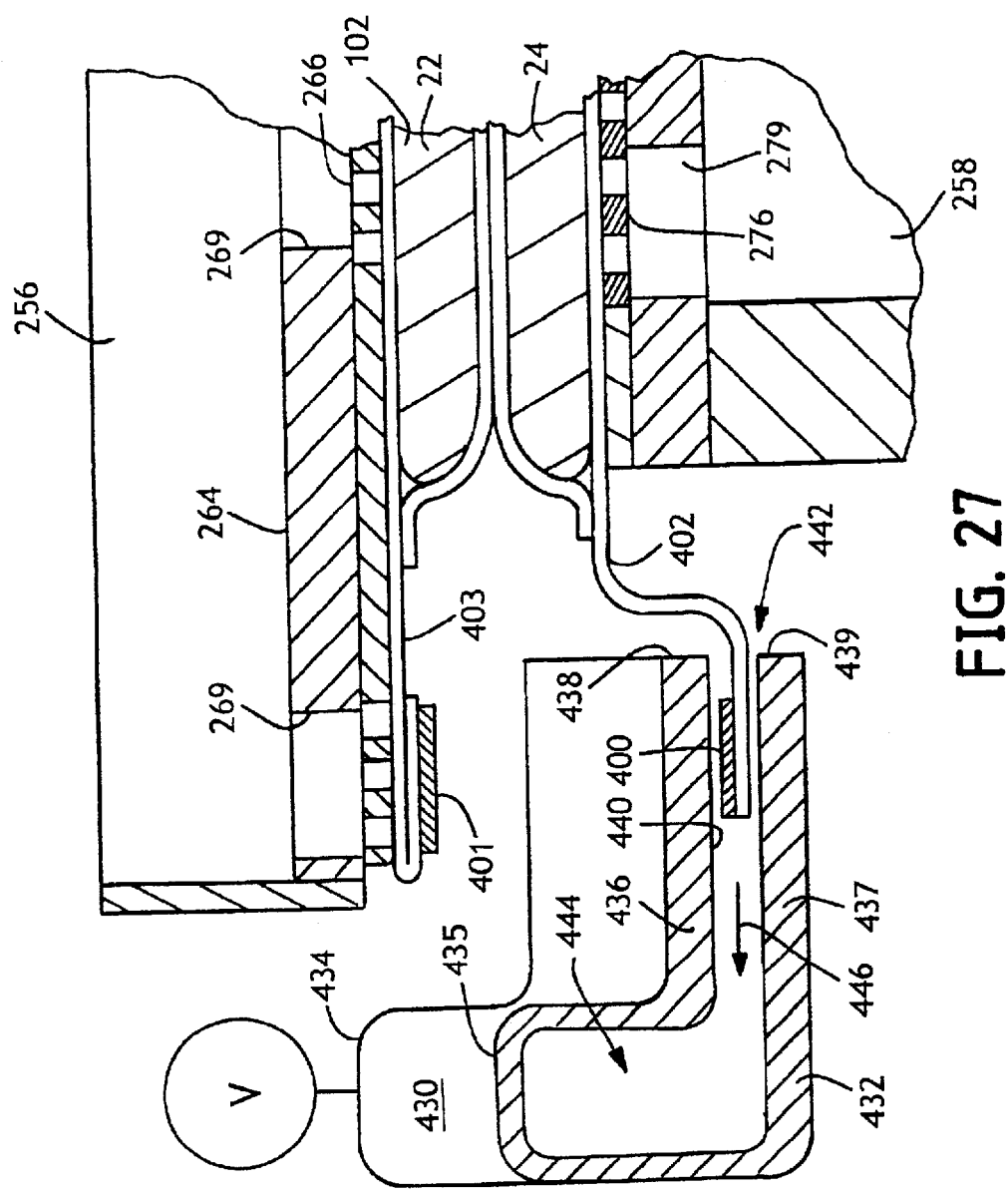

With reference to FIGS. 25–27, the fluid flow devices 430 can each comprise an elongated body 432 which can be integrally formed or comprise separate elements bonded together. The elongated body 432 defines an upstream end 434 and an opposite downstream end 435 (FIGS. 27–29), the latter being downstream of the former in relation to the machine direction 108. Each fluid flow device 430 can be mounted on the alignment conveyors 256 or 258 or other suitable frame structures (not shown). The elongated body 432 can comprise opposed walls 436 and 437 which define therebetween an internal passageway 440. The walls 436 and 437 can have respective terminal ends 438 and 439 disposed toward the machine center line which together define an entry slot 442 in fluid communication with the internal passageway 440. The entry slot 442 connects the internal passageway 440 with the space surrounding the elongated body 432. The end of the passageway 440 opposite the entry slot 442 defines a fluid discharge region 444.

The elongated body 432 can be formed of any suitable material. Portions or surfaces that come into contact with the training pant 102 are desirably formed of a low friction material. Suitable low friction materials or coatings include but are not limited to: stainless steel; low carbon steel; polycarbonate material; teflon; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like.

Each fluid flow device 430 can be configured to establish a flow of fluid through the internal passageway 440 in the direction of arrows 446. For example, the fluid discharge region 444 can be connected to a vacuum source V as illustrated in FIGS. 25–27 to draw fluid through the internal passageway 440. The fluid discharge region 444 can be operatively connected to a vacuum source V by any suitable means, such as ports (not shown) extending through the elongated body 432. The level of vacuum within the fluid discharge region 444 can vary depending upon the application, for example, from 1 to about 10 inches of water or greater below atmospheric pressure, and more particularly from about 2 to about 8 inches of water or greater below atmospheric pressure. Alternatively, pressurized fluid can be directed into the internal passageway 440 to establish a flow of fluid through the passageway. Still alternatively, a combination of a vacuum source and a pressurized fluid source can be employed.

The induced air flow 446 through the passageway 440 can pull a side panel outward from the machine center line, and desirably at least partially into the passageway, thereby straightening the side panel. The width of the entry slot 442 and passageway 440 can be selected to accommodate a side panel and allow fluid flow through the slot, such as a width of about 5 millimeters or more, particularly about 10 millimeters or more, and a width of about 20 millimeters or less, particularly about 15 millimeters or less. The walls 436 and 437 can converge or diverge relative to one another, or be generally parallel as illustrated. The depth of the passageway 440 measured between the entry slot 442 and the fluid discharge region 444 will depend upon the application and the amount of material to be fed into the internal passageway, and may by way of illustration be about 10 to about 20 centimeters. The entry slot 442 can have any suitable length in the machine direction, such as about 0.3 to about 4 meters, for example about 1 meter. The entry slot 442 and passageway 440 extend over at least a portion of the length of the elongated body 432.

As seen by comparing FIGS. 25, 26 and 27, the fluid flow devices 430 can be oriented such that they each form an angle relative to the pant transport plane. More specifically, each fluid flow device 430 defines an axis extending generally between the upstream and downstream ends 434 and 435, and the axis can form an angle relative to the pant transport plane, for example, of about 1 degree or more, such as about 1 to about 20 degrees, particularly about 1 to about 10 degrees. Depending upon the desired functionality, the fluid flow devices 430 can be inclined relative to the pant transport plane, such that the fluid flow devices are angled toward the pant transport plane at downstream machine direction locations, or declined relative to the pant transport plane, such that the fluid flow devices are angled away from the pant transport plane at downstream machine direction locations. Stated differently, the fluid flow devices 430 define a side panel transport path, over which the side panels are transported as they move in the machine direction 108 within the fluid flow devices. Owing to the fact that the fluid flow devices 430 are angled with respect to the pant transport plane, the side panel transport path defined by the fluid flow devices is also angled with respect to the pant transport plane. Consequently, the fluid flow devices 430 can move the laterally outward portions of the first side panels 402 in the z-direction perpendicular to the pant transport plane, and can also move laterally outer portions of the side panels laterally inward toward the machine center line, as the side panels are transported in the machine direction 108 within the fluid flow devices. In the embodiment illustrated in FIGS. 25–27, the fluid flow devices 430 are declined relative to the pant transport plane. The entry slot 442 is approximately level with the conveyor belt 276 of the lower conveyor 258 in FIG. 25, but is significantly lower at the downstream position depicted in FIG. 27.

As the training pant 102 is transported in the machine direction 108, the first side panels 402 can be introduced into the fluid flow devices 430 in any suitable manner. For example, the side panels 402 can be transported to the fluid flow devices 430 using transition plates (not shown) and air knives, air bars, air nozzles or the like to maintain the side panels on or against the transition plates. The side panels 402 can be guided into the entry slots 442 or can enter the passageways 440 through openings in the elongated body 432 at the upstream ends 434 of the fluid flow devices 430.

With specific reference to FIG. 25, as the side panel 402 is drawn into the passageway 440, it can be pulled directly perpendicular away from the machine center line. The side panel 402 can thus be extended and straightened with minimal drag in the machine direction 108. As the training pant 102 advances to the machine direction position of FIG. 26, the laterally outward portions of the side panels 402 follow the declined angle of the fluid flow devices 430. The laterally outward portions including the first fastening components 400 advance transversely inward toward the machine center line. Desirably, the distal edges of the side panels 402 can remain generally parallel to the machine center line. Continuing to the machine direction position of FIG. 27, the laterally outward portions of the first side panels 402 can move transversely inward to the point where the first fastening component 400 is aligned in the cross-machine direction with its corresponding second fastening component 401. The second fastening component 401 as illustrated was previously inverted and held in place by the upper alignment conveyor 256. Of course, the fluid flow devices 430 could alternatively be maintained at a constant horizontal position while the conveyors 256 and 258 angle away from the fluid flow devices.

The fluid flow devices 430 can be positioned on opposite sides of the machine center line at the same machine direction 108 location. Alternatively, the fluid flow devices 430 can be staggered in the machine direction 108 to allow for cross-machine direction movement-control devices or operations used in combination with a single fluid flow device. The cross-machine direction movement-control devices or operations can comprise any suitable devices or operations which maintain cross-machine direction control of the training pant 102 during operation of the fluid flow device.

Figure 28:
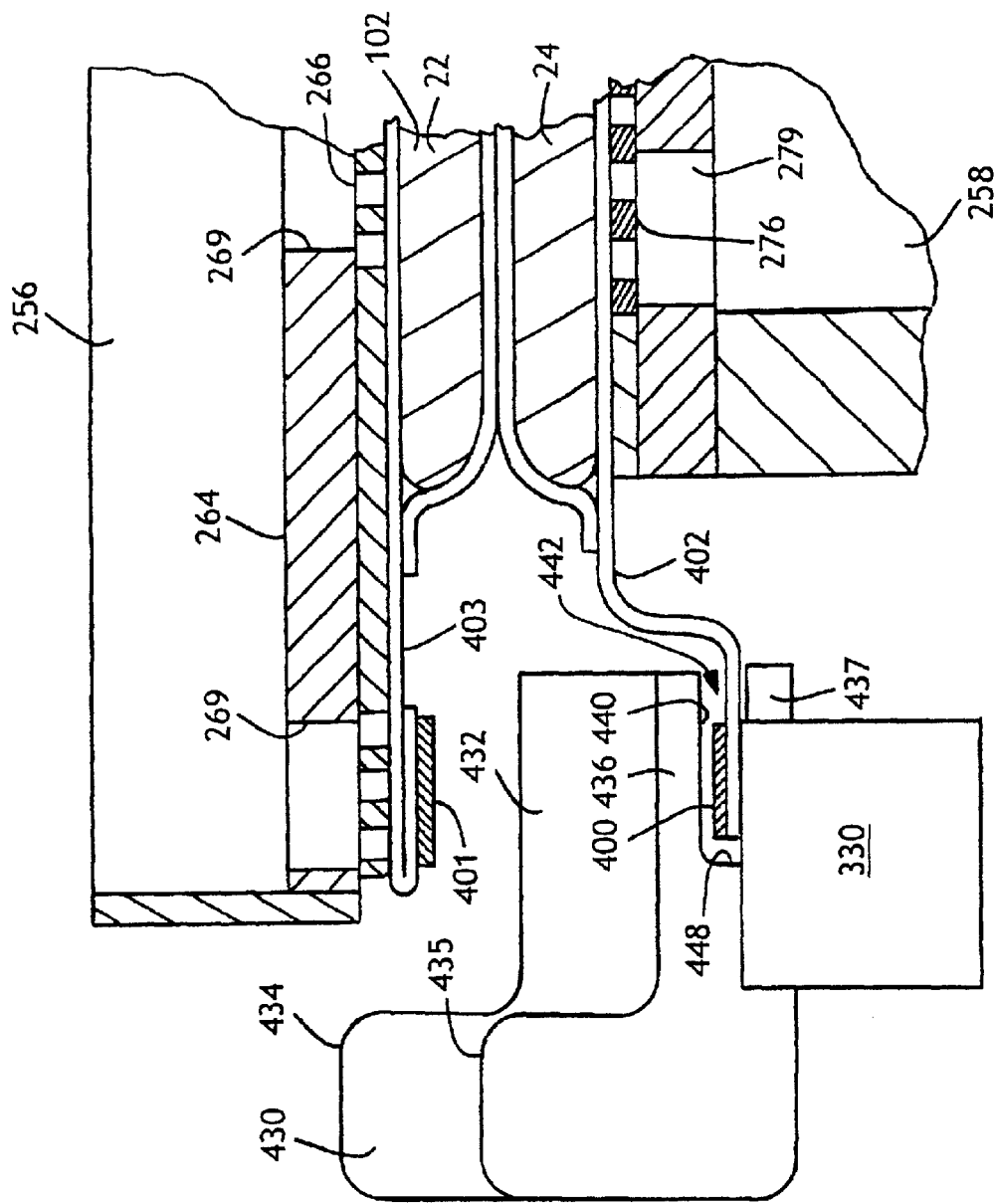
Figure 29:
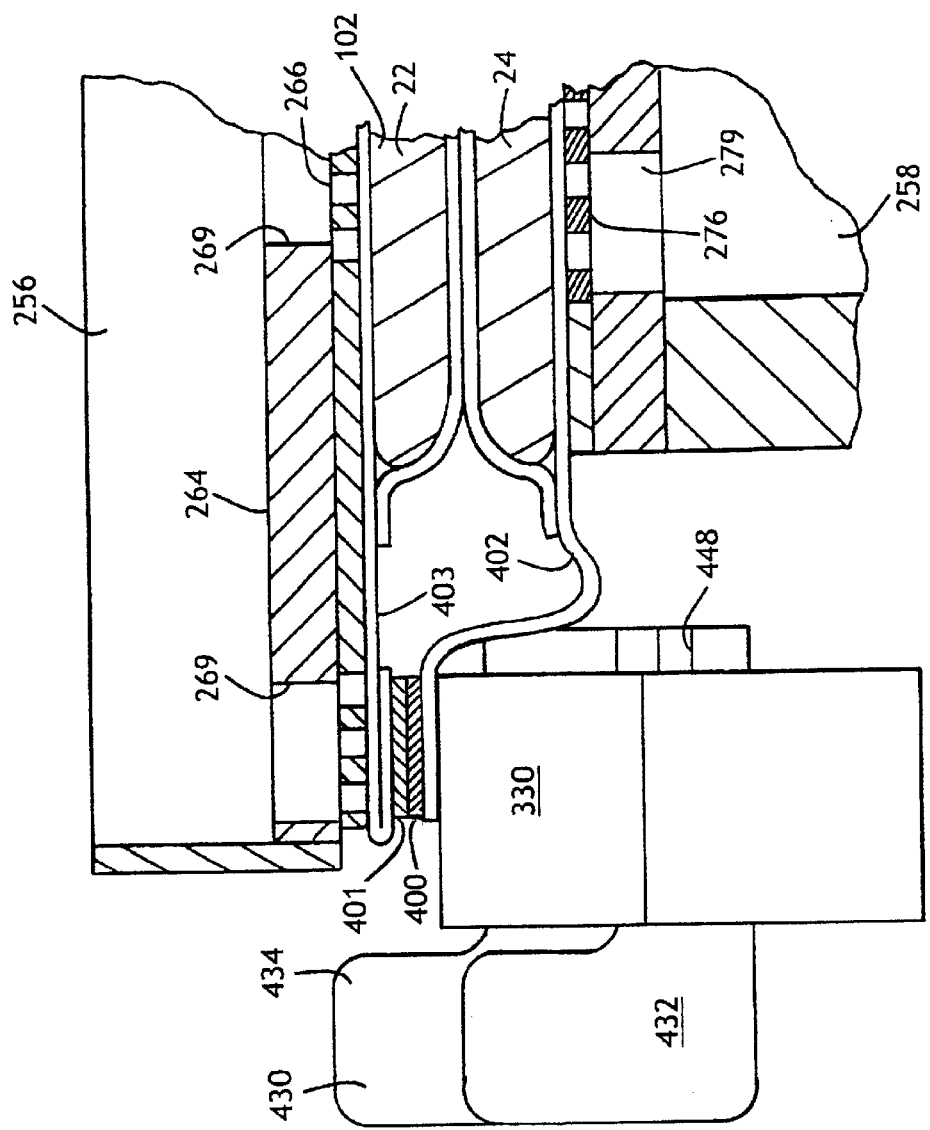

Upon reaching the downstream ends 435 of the fluid flow devices 430, the side panels 402 can be transitioned from the fluid flow devices onto the side panel transfer devices 330 (FIG. 28). The downstream ends 435 of the elongated bodies 432 can define openings 438 through which the laterally outward portions of the side panels 402 can exit the fluid flow devices 430. The vacuum from the side panel transfer devices 330 can pull the side panels 402 onto the side panel transfer devices. Depending on the desired configuration, the top wall 436 of the fluid flow device 430 can extend downstream of the bottom wall 437 and over a portion of the side panel transfer device 330. The top wall 436 in such an embodiment can include apertures (not shown) to provide make-up air for the side panel transfer device 330. From this point forward, the process depicted in FIGS. 28–29 can be similar to that depicted in FIGS. 23–24. Thus the fastening components are shown engaged in FIG. 29, after the first side panel 402 and first fastening component 400 were elevated in the z-direction by the side panel transfer devices. While lower side panels are shown within the fluid flow devices 430, it should be understood that upper side panels or any combination of upper and/or lower side panels can be repositioned using fluid flow devices.

Figure 30:
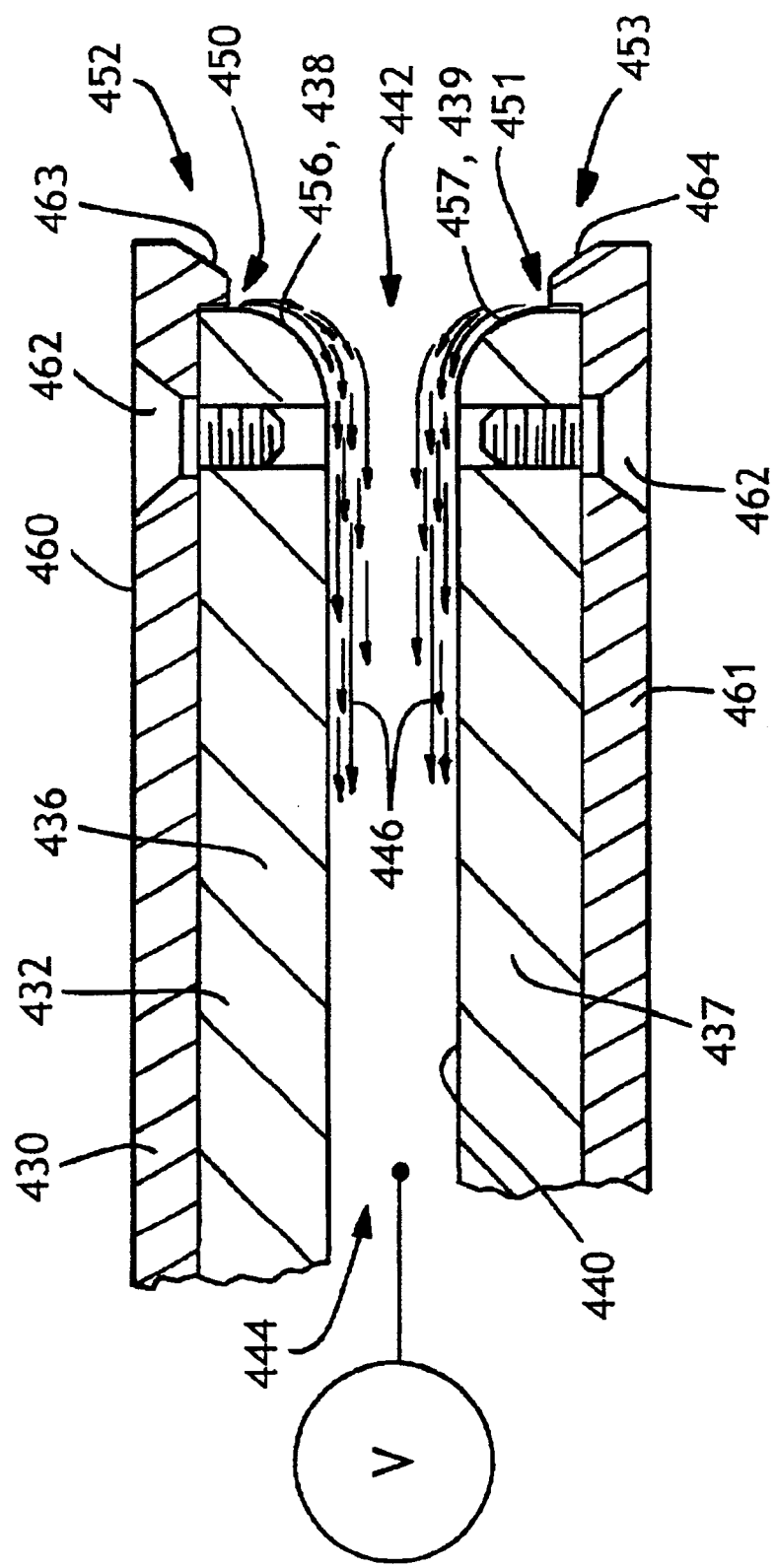
FIG. 30 illustrates an enlarged section view of a portion of an alternative fluid flow device.

Portions of an alternative fluid flow device 430 are depicted in FIG. 30. The fluid flow device 430 comprises an elongated body 432 with interior walls 436 and 437. The elongated body 432 and walls 436 and 437 define an internal passageway 440, an entry slot 442 and a fluid discharge region 444. The illustrated fluid flow device 430 comprises upper and lower nozzles 450 and 451 that direct pressurized fluid into the internal passageway 440 to create a flow of fluid in the direction of arrows 446. The nozzles 450 and 451 can be supplied with pressurized fluid from any suitable source or sources. The fluid discharge region 444 can be exhausted to atmosphere or operatively connected to a vacuum source V.

The type and location of the nozzles 450 and 451 can assume any desired form suitable for the particular application. For example, the nozzles can comprise air jets, air knives, air bars or the like. Additionally, the nozzles can be integrated within the walls 436 and 437 and/or passageway 440, disposed near the entry slot 442, and/or disposed outside the passageway. In one particular embodiment, the fluid flow device 430 comprises one or more air knives 452 and 453 disposed on opposite sides of the entry slot 442 to direct pressurized fluid into the internal passageway 440. In one particularly desirable embodiment, each air knife 452 and 453 comprises a nozzle 450 or 451 and a Coanda surface 456 or 457 that is curved to direct fluid from the nozzle into the internal passageway 440. The air knives 452 and 453 can comprise separate elements attached to the fluid flow devices 430 or integral or partially-integrated components of the fluid flow devices.

Figure 31:
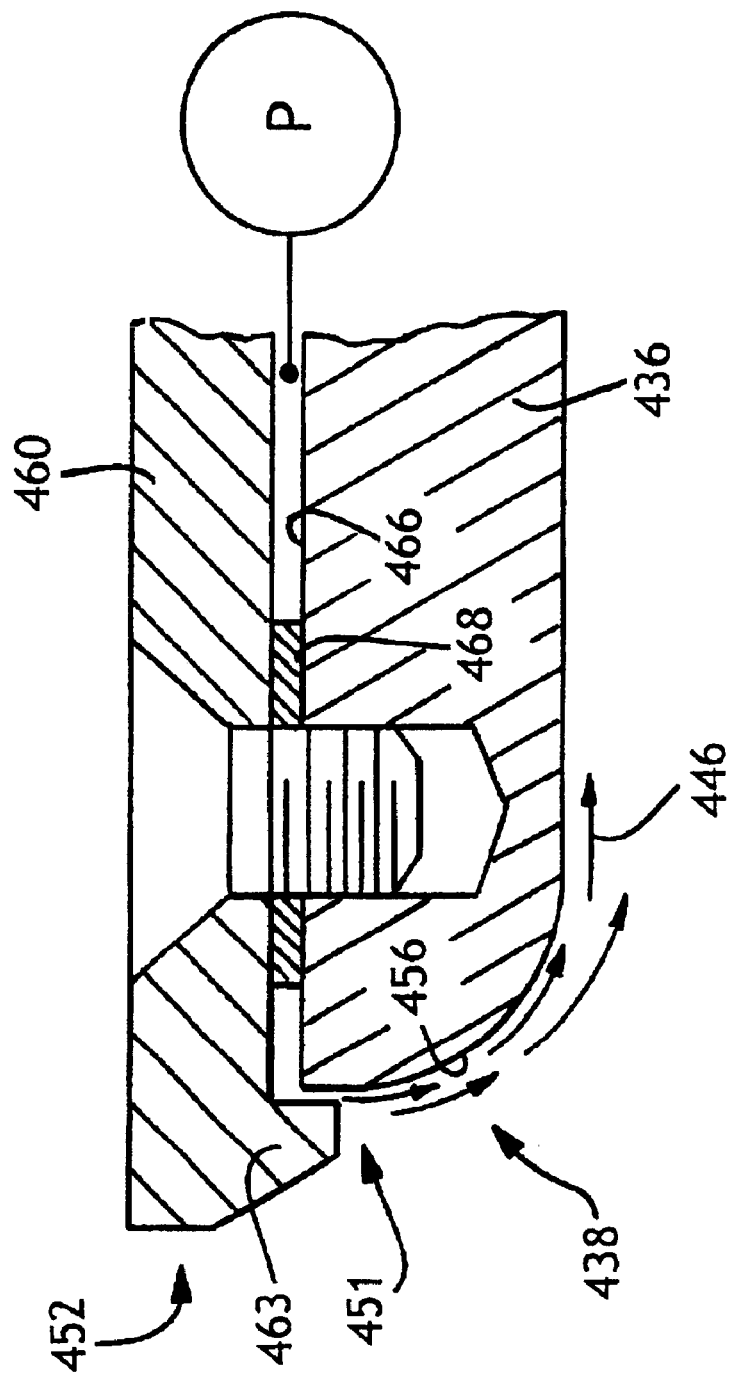
FIG. 31 illustrates an enlarged section view of a portion of the fluid flow device of FIG. 30.

In the illustrated embodiment, the fluid flow devices 430 comprise a first cap 460 associated with the first wall 436 and a second cap 461 associated with the second wall 437. The caps 460 and 461 can be attached to the walls 436 and 437 with suitable fasteners 462. While the caps 460 and 461 may assume a wide variety of configurations, each illustrated cap includes a head 463 and 464 that projects slightly beyond and over a terminal end 438 and 439 of the associated wall 436 and 437. The spacing between the cap heads 463 and 464 and the terminal ends 438 and 439 of the walls 436 and 437 form thin nozzles 450 and 451. Pressurized fluid can be provided to the nozzles 450 and 451 by any suitable means. In one particular embodiment separately illustrated in FIG. 31, the cap 460 can be spaced apart slightly from the wall 436 to form a channel 466 therebetween. The channel 466 is suitably sized to permit the transport of pressurized fluid from a source of pressurized fluid P to the nozzle 451. The channel 466 can be formed by machining grooves in the wall 436 and/or cap 460 or by including thin spacers 468 between the walls and caps.

As viewed in FIG. 30, the nozzles 450 and 451 expel fluid at an angle substantially perpendicular to the plane of the internal passageway 440 and substantially perpendicular to the pant transport plane. The opposed nozzles 450 and 451 in the embodiment of the FIG. 30 expel fluid toward one another. For purposes of the present application, the direction fluid is expelled from a nozzle 450 or 451 at the moment when an air knife 452 or 453 is activated will be referred to as the nozzle flow direction. In relation to FIG. 30, the nozzle flow direction of the upper air knife 452 is toward the bottom of the figure and the nozzle flow direction of the lower air knife 453 is toward the top of the figure.

The air knives 452 and 453 can each comprise a surface 456 and 457 adjacent and extending beyond the nozzle 450 and 451, which surface will be referred to herein as a Coanda surface. The Coanda surface 456 and 457 is the surface that the air from the nozzle 450 and 451 will follow under normal operating conditions. In the illustrated embodiment, the terminal ends 438 and 439 of the walls 436 and 437 have smooth, curved cross-sectional profiles and form the Coanda surfaces 456 and 457. In this particular embodiment, the Coanda surfaces 456 and 457 are curved relative to the nozzle flow direction. Specifically, the illustrated Coanda surfaces 456 and 457 in cross section gradually curve away from the nozzles 450 and 451 and heads 463 and 464 of the caps 460 and 461 forming 90 degree curved portions. The Coanda surfaces 456 and 457 can have any desired curvature in cross section suitable for a particular application, such as 0 to about 270 degrees, particularly from 0 to about 180 degrees, and more particularly about 20 to about 90 degrees. The curvature of the Coanda surfaces 456 and 457 can also represent the angle that the resulting sheet of air bends from the nozzle flow direction. The Coanda surfaces 456 and 457 can employ a variety of configurations beyond those specifically illustrated herein, such as a plurality of smaller curved portions separated by generally planar portions; larger or smaller radius curved portions; a generally planar portion between the nozzle and the initial curved portion; a completely curved surface; or the like. Moreover, the air knives 452 and 453 described herein can employ integral or separate plena, caps and/or Coanda surfaces. Alternatively, the air knife can be a separate component disposed on or disposed near the lower conveyor 258.

In operation, compressed air is delivered from a pressurized fluid source P via channels 466 or other suitable means and expelled from each nozzle 450 and 451 in the form of a jet. Due to the nozzle configuration, the jet forms an air sheet that further entrains ambient air. Based on the Coanda effect, which is sometimes referred to as the wall-attachment principle, the presence of the Coanda surface 456 and 457 creates a differential in pressure across the two sides of the air sheet causing the sheet to attach to and follow the curved Coanda surface. Once the side panels 402 or 403 are positioned in proximity to the entry slots 442, the side panels will be drawn into the internal passageways 440 by the laminar flow of the air sheets over the Coanda surfaces 456 and 457.

The air knives 452 and 453 can be formed of stainless steel, aluminum, or other suitable materials. Typical operating ranges for the air supply source are about 1.4 to about 6.9 bars (20–100 pounds per square inch) with air consumption of about 37 to about 116 standard liters per minute (SLPM) (1.3–4.1 standard cubic feet per minute) per 25 millimeter length of nozzle. For example, the air supply pressure can be 2.8 bars (40 psi) with air consumption of about 57 SLPM (2 SCFM). The aperture of the nozzle 450 and 451 can be adjusted with shims to obtain the desired air velocity. In one particular embodiment, the nozzle 450 and 451 opening is about 0.05 millimeters (0.002 inch). As an alternative to a continuous nozzle opening, the nozzle can comprise a different configuration such as a large number of individual, closely spaced apertures. The length dimension of an air knife 452 and 453 can be oriented generally parallel to the axis of the fluid flow device 430, with the nozzle 450 and 451 extending over part or all of the length dimension. The air knife 452 and 453 can have any desired length dimension, such as about 0.1 to about 1 meter, for example about 0.6 to about 0.7 meter. Suitable air knives are available from various commercial vendors, such as ITW Vortec, or EXAIR Corporation, both of Cincinnati, Ohio U.S.A.

Figure 32:
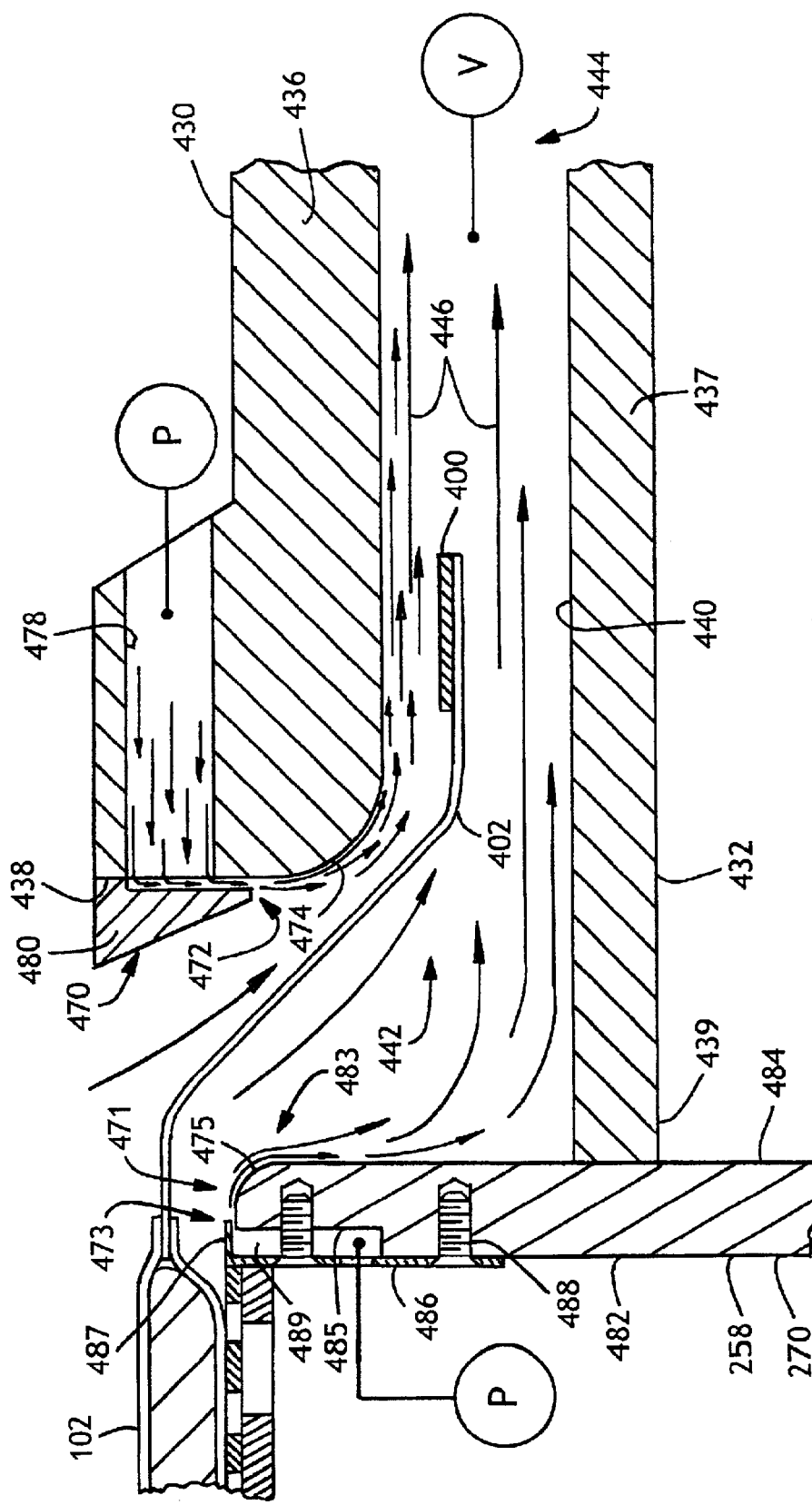
Figure 32 illustrates a section view of a further alternative embodiment of a method and apparatus for making garments.

Portions of another alternative fluid flow device 430 for handling garment side panels 402 are depicted in FIG. 32. The fluid flow device 430 comprises an elongated body 432 with interior walls 436 and 437. The elongated body 432 and walls 436 and 437 define an internal passageway 440, an entry slot 442 to the passageway, and a fluid discharge region 444. The illustrated fluid flow device 430 is operatively associated with a pair of air knives 470 and 471 adapted to direct pressurized fluid into the internal passageway 440 to create a flow of fluid in the direction of arrows 446. The illustrated air knives 470 and 471 comprise nozzles 472 and 473 and Coanda surfaces 474 and 475. The nozzles 472 and 473 can be supplied with pressurized fluid from any suitable source or sources P. The fluid discharge region 444 can be exhausted to atmosphere or operatively connected to a vacuum source V.

The air knife 470 associated with an upper portion of the entry slot 442 comprises a nozzle 472 and a curved Coanda surface 474 which operate to establish a flow of fluid into the internal passageway 440 from above the passageway. In the illustrated embodiment, the interior wall 436 above the passageway defines a terminal end 438 disposed toward the machine center line. The terminal end 438 includes one portion defining the Coanda surface 474 and an adjacent portion defining a channel 478. The channel 478 can be operatively connected with a source of pressurized fluid P. The portion of the terminal end 438 defining the Coanda surface 474 is illustrated with a smooth, curved cross-sectional profile, although the Coanda surface may take a variety of other shapes as referenced previously.

A cap 480 can be disposed on the portion of the terminal end 438 defining the channel 478 and can be attached thereto with any suitable fasteners (not shown). The cap 480 can be positioned over the channel 478 and spaced slightly from the terminal end 438 to form a thin nozzle 472 between the cap and the terminal end. The nozzle 472 can be in fluid communication with the channel 478, and hence with the pressurized fluid source P. The nozzle flow direction of this air knife 470 is toward the bottom of the figure, and the Coanda surface 474 is curved relative to the nozzle flow direction.

The air knife 471 associated with the lower portion of the entry slot 442 comprises a nozzle 473 and a curved Coanda surface 475 which operate to establish a flow of fluid into the internal passageway 440 from beneath the passageway. In the illustrated embodiment, this air knife 471 is formed as a partially-integrated component of the lower alignment conveyor 258. In particular, the conveyor 258 can include a frame structure 270 having a support element 482 disposed between the entry slot 442 and the machine center line. The support element 482 can form, for example, a side wall of the frame structure 270. The illustrated support element 482 defines a terminal end 483 disposed near the pant transport path and an outer surface 484 directed away from the machine center line. The terminal end 483 includes one portion defining a Coanda surface 475 and an adjacent recessed portion 485. The portion of the terminal end 483 defining the Coanda surface 475 is illustrated with a smooth, curved cross-sectional profile, although the Coanda surface may take a variety of other shapes as referenced previously.

A cap 486 can be attached to the support element 482 using any suitable fasteners, such as screws 488. The cap 486 can be spaced slightly from the terminal end 483 to form a channel 489 between the cap and the support element 482. The illustrated cap 486 includes a head 487 that projects slightly beyond and over the terminal end 483 of the support element 482. The spacing between the cap head 487 and the terminal end 483 of the support element 482 forms a thin nozzle 473, which is in fluid communication with the channel 489. The channel 489 and hence the nozzle 473 can be operatively connected with a source of pressurized fluid P, which can be isolated from vacuum for the lower conveyor 258. The nozzle flow direction of this air knife 471 is toward the right side of the figure, and the Coanda surface 475 is curved relative to the nozzle flow direction.

The fluid jet expelled from the nozzle 473 forms an air sheet that further entrains ambient air. The air sheet attaches to and follows the curved Coanda surface 475. In the embodiment of FIG. 32, the interior wall 437 beneath the passageway 440 defines a terminal end 439 disposed in sealing contact with the frame structure 270 of the lower alignment conveyor 258. As such, fluid from the nozzle 473 passes through the internal passageway 440, moving along the outer surface 484 and lower wall 437.

In operation, the training pant 102 is transported in the machine direction 108 with the side panels 402 positioned within the fluid flow devices 430. The fluid flow devices 430 can be angled with respect to the pant transport plane to shape the side panels in the z-direction. Alternatively, the fluid flow devices 430 can be oriented parallel to the pant transport plane and used simply to transport the side panels in the machine direction 108 with minimal friction. The side panels 402 are drawn into the internal passageway 440 and extended in the cross-machine direction due to fluid flow through the passageway 440. Moreover, the fluid path controls and stabilizes the position of the side panels 402. The side panels 402 will in essence be floating either against a boundary layer of air or between two boundary layers of air in a near frictionless path. Friction is particularly reduced around corners which the side panels would encounter when the side panels are being shaped in the z-direction. The reduced friction leads to less skewing of the side panels as they move in the machine direction 108. The amount of fluid flow through the passageway 440 will be enhanced by utilizing one or both of the air knives, by operatively connecting the discharge region to a vacuum source, or by operating the fluid flow devices with both positive and negative pressure devices.

Figure 33:
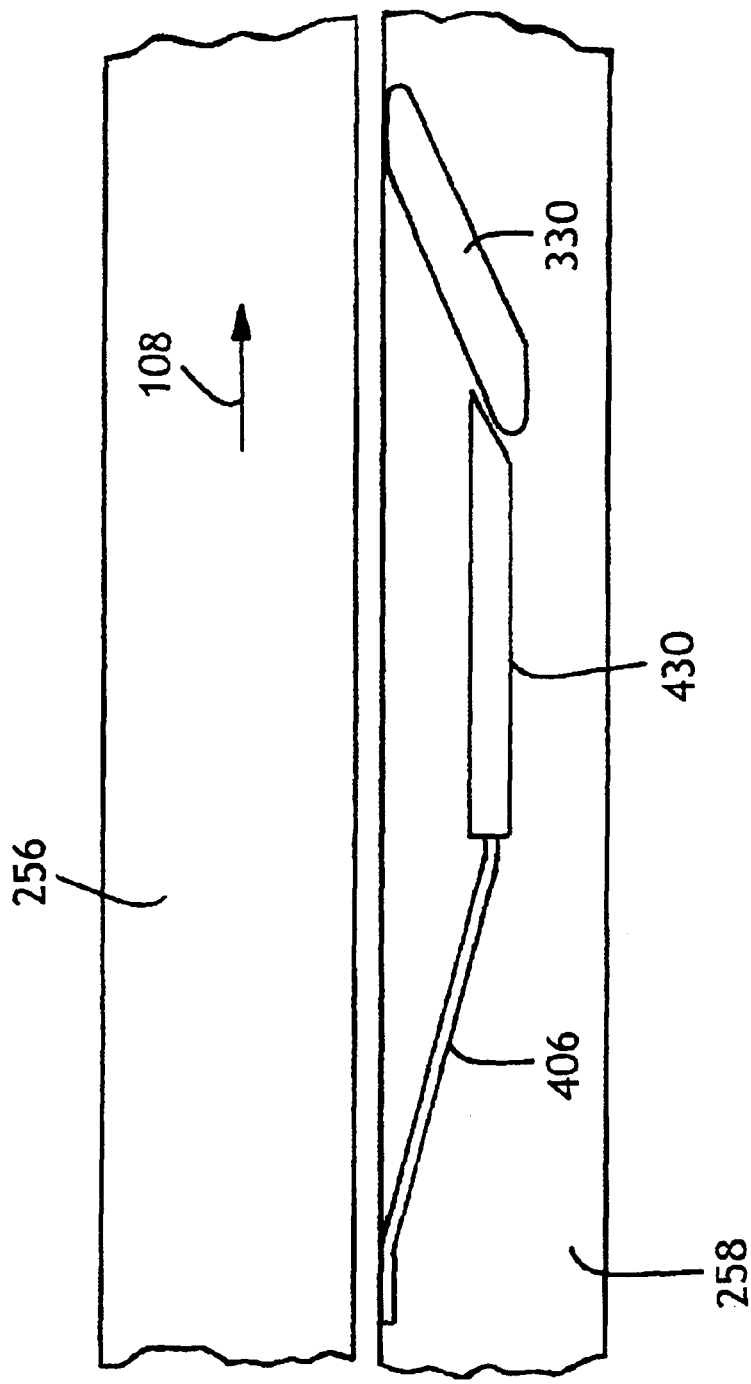
FIG. 33 illustrates a side view of an alternative embodiment of the present method and apparatus for positioning garment side panels, including a fluid flow device oriented parallel to the pant transport plane.

As noted above, the fluid flow devices 430 can also be oriented parallel to the pant transport plane. For example, an alternative embodiment of a method and apparatus for positioning garment side panels 402 is schematically illustrated in FIG. 33. FIG. 33 is a side view including upper and lower conveyors 256 and 258 adapted to transport a pant in the machine direction 108. The conveyors 256 and 258 define a pant transport plane between the conveyors and a z-direction perpendicular to the pant transport plane. A first device 406 can initially be used to transport or move the side panels 402 (not shown in FIG. 33) in the z-direction away from the pant transport plane as the side panels are transported in the machine direction 108. By way of example, the first device 406 can comprise a curved guide plate 406 as described in relation to FIGS. 21–23, an angled fluid flow device as described in relation to FIGS. 25–28, or any other suitable device for transporting the side panels in the z-direction. Thereafter, the side panels 402 can be positioned within fluid flow devices 430 that are essentially parallel to the pant transport plane. The parallel fluid flow devices 430 permit the side panels to be transported in the machine direction while at least the laterally outward portions of the side panels are disposed at z-direction positions displaced from the pant transport plane. The parallel fluid flow devices 430 can minimize friction and assist in straightening the side panels 402, for example, eliminating skew which may have been introduced by the first device 406. Subsequently, the side panels 402 can be transitioned onto side panel transfer devices 330 for subsequent processing, as described previously.

The parallel fluid flow devices 430 depicted in FIG. 33 are displaced from the pant transport plane. More specifically, the internal passageways 440 (not shown in FIG. 33) of the fluid flow devices 430 are displaced in the z-direction outside the pant transport plane. For purposes of the present invention, an internal passageway of a fluid flow device is considered to be displaced in the z-direction outside the pant transport plane when a portion of the internal passageway where the side panel travels is positioned completely above or below the pant transport plane. By way of illustration, the portion of the internal passageway 440 depicted in FIG. 27 is displaced from the pant transport plane, although the specific fluid flow device 430 in FIG. 27 is angled relative to the pant transport plane rather than being parallel as shown in FIG. 33. Also for purposes of the present invention, the wall 436 or 437 that defines the internal passageway 440 and is closest to the pant transport plane will be referred to as a reference surface. In FIG. 27, the upper wall 436 is closest to the pant transport plane and is deemed the reference surface. In particular embodiments, the reference surface can be displaced from the pant transport plane in the z-direction by greater than 0 millimeters, particularly greater than about 10 millimeters. Also in particular embodiments, the reference surface can be displaced from the pant transport plane in the z-direction by less than about 50 millimeters, particularly less than about 25 millimeters. The desired amount of displacement will depend upon the desired application and also the cross-machine direction spacing of the fluid flow devices 430 from the conveyors 256 and 258. For determining the distance a reference surface is displaced from the pant transport plane, the conveyor surface or other surface supporting the central portion of the pant composite structure 33 (FIGS. 4–6) will be considered the pant transport plane. For present purposes, the surface of the lower conveyor belt 276 in FIG. 27 is considered to define the pant transport plane.

As can be seen from the foregoing, the fluid flow devices 430 can assume a wide variety of shapes and configurations for positioning garment side panels. In relation to the machine direction, the fluid flow devices 430 can be parallel to the pant transport plane or oriented such that they form an angle relative to the pant transport plane. The fluid flow devices 430 can also include a combination of different segments which can be parallel and/or form one or more different angles relative to the pant transport plane. In relation to the cross-machine direction, the internal passageways 440 can comprise planar segments, curved segments or a combination of planar and curved segments. The entry slots 442 can be disposed at the same z-direction elevation or at different elevations as the internal passageways 440. Hence, the internal passageways can assume any desired multi-faceted shape to transport and/or displace the side panels.

The side panel transfer devices 330 can alternatively comprise other devices for sequentially or simultaneously affecting upward and inward relative movement of the laterally outward portions of the back side panel 134 and the initially inward-facing fasteners 82 and 83 disposed thereon. By way of illustration, suitable side panel transfer devices 330 can alternatively comprise disks or wheels, either aligned in the machine direction 108 or canted and/or tilted relative thereto so that the disks or wheels raise the side panels and nip the fasteners together. Suitable wheel devices can, but need not, be timed elliptical wheels, and can comprise vacuum or traction surface wheels or the like. Still alternatively, the side panel transfer devices 330 can comprise 4-bar linkage mechanisms carrying a panel engagement head which contacts the back side panel 134 to raise the panel relative to the plane of the lower alignment conveyor 258. The rotary motion provided by the 4-bar linkage can allow the panel engagement head to raise a back side panel 134 relative to the lower alignment conveyor 258, with the back side panel being allowed to slip off the inward edge of the panel engagement head. A drive mechanism for the 4-bar linkage can be programmed to vary the angular velocity of the panel-engagement head such that its velocity in the machine direction 108 matches the speed of the back side panel 134 while the panel-engagement head is in contact with the back side panel. Alternatively, the angular velocity of the panel-engagement head can be matched with the velocity of the side panel using a cam gearbox, non-circular gearing, or the like. Such devices could further comprise a feedback system to register the panel-engagement head to the back side panel 134. In yet another alternative embodiment, the side panel transfer devices 330 can comprise folding boards or folding skis to provide sequential or simultaneous inward and upward relative movement of the laterally outward portions of the back side panels 134 and the inwardly directed fasteners 82 and 83.

In the illustrated process, the initially outward-facing fasteners 84 and 85 are directed upward against an upper alignment conveyor 256. Alternatively, the process could be inverted such that the initially outward-facing fasteners 84 and 85 are directed downward against a lower fastener conveyor or surface (not shown). As mentioned above, the laterally outward portions of the side panels which carry the initially outward-facing fasteners may need mechanical or fluid assist to initiate inward folding. Additionally, other changes, as will readily be apparent to those skilled in the art, may be required, such as changes to the width of the conveyors, orientation of fluid devices, and insertion of skid plates to maintain the position of side panels.

Thus, the methods and apparatus disclosed herein can provide precise lap seams at high-speeds in garments such as training pants 20. From folded products having side panels with both initially outward-facing fasteners and initially inward-facing fasteners, the side panels can be separated to provide clearance for inward folding of one pair of side panels, the side panels with the initially outward-facing fasteners can be inwardly folded 180 degrees, and the initially inward-facing fasteners can be moved transversely inward to the position of the previously folded, initially outward-facing fasteners.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method for positioning side panels during manufacture of a pant, comprising:

transporting a pant in a machine direction thus defining a pant transport plane and a z-direction perpendicular to the pant transport plane, the pant comprising at least one waist region comprising opposite side panels; and positioning the side panels within fluid flow devices, each fluid flow device defining an upstream end, an opposite downstream end, an axis extending generally between the upstream and downstream ends and a side panel transport path, the axis and side panel transport path being non-parallel to the pant transport plane;

whereby at least laterally outward portions of the side panels move in the z-direction while the pant is transported in the machine direction and the side panels reside within the fluid flow devices.

2. The method of claim 1, further comprising allowing at least the laterally outward portions of the side panels to move inward toward a machine center line while the pant is transported in the machine direction and the side panels reside within the fluid flow devices.

3. The method of claim 1, wherein positioning the side panels within fluid flow devices comprises inserting the side panels in passageways having a flow of fluid from an entry slot toward a discharge region.

4. A method for positioning side panels during manufacture of a pant, comprising:

transporting a pant in a machine direction thus defining a pant transport plane and a z-direction perpendicular to the pant transport plane, the pant comprising at least one waist region comprising opposite side panels; and positioning the side panels within fluid flow devices located on opposite sides of a machine center line, each fluid flow device defining an upstream end, an opposite downstream end, an axis extending generally between the upstream and downstream ends, the axis being non-parallel to the pant transport plane such that at least laterally outward portions of the side panels move in the z-direction and toward the machine center line while the pant is transported in the machine direction and the side panels reside within the fluid flow devices.

5. The method of claim 4, wherein the pant comprises opposite first and second waist regions, the first waist region comprising first side panels and the second waist region comprising second side panels, the first and second side panels each comprising fastening components, and laterally outward portions of the first side panels are moved inward such that the fastening components disposed on the first side panels are aligned in a cross machine direction with the fastening components disposed on the second side panels.

6. The method of claim 4, wherein positioning the side panels within fluid flow devices comprises inserting the side panels in passageways having a flow of fluid from an entry slot toward a discharge region.

7. A method for making a prefastened and refastenable pant, comprising:

transporting a folded pant in a machine direction thus defining a pant transport plane and a z-direction perpendicular to the pant transport plane, the folded pant having opposite first and second waist regions in facing relation, the first waist region comprising first side panels and the second waist region comprising second side panels, the first side panels comprising initially inward-facing fastening components, and the second side panels comprising initially outward-facing fastening components;

inverting the initially outward-facing fastening components;

transporting the first side panels within fluid flow devices in the z-direction away from the pant transport plane while the folded pant is transported in the machine direction;

transferring the first side panels from the fluid flow devices to side panel transfer devices;

transporting the first side panels on the side panel transfer devices in the z-direction toward the pant transport plane while the folded pant is transported in the machine direction; and engaging the initially inward-facing and initially outward-facing fastening components.

8. The method of claim 7, wherein the fluid flow devices and side panel transfer devices are angled in opposite directions relative to the pant transport plane.

9. The method of claim 8, wherein the fluid flow devices are declined relative to the pant transport plane and the side panel transport devices are inclined relative to the pant transport plane.

10. The method of claim 7, wherein laterally outward portions of the first side panels are moved inward such that the initially inward-facing fastening components are aligned in a cross machine direction with the inverted initially outward-facing fastening components.

11. The method of claim 7, further comprising maintaining the first side panels at a constant cross-machine direction position while the folded pant is transported in the machine direction and the first side panels reside on the side panel transfer devices.

12. The method of claim 7, wherein the initially inward-facing fastening components are separated from one another by an initial distance and the initially outward-facing fastening components are separated from one another by substantially the same initial distance.-

13. A method for positioning side panels during manufacture of a pant, comprising:

transporting a pant in a machine direction thus defining a pant transport plane and a z-direction perpendicular to the pant transport plane, the pant comprising at least one waist region comprising opposite side panels;

transporting at least laterally outward portions of the side panels in the z-direction away from the pant transport plane while the pant is transported in the machine direction;

positioning the side panels within internal passageways of fluid flow devices located on opposite sides of a machine center line, the internal passageways displaced in the z-direction outside the pant transport plane; and transporting the side panels within the internal passageways while at least laterally outward portions of the side panels reside outside the pant transport plane and the pant is transported in the machine direction.

14. The method of claim 13, wherein each fluid flow device defines a side panel transport path that is at least in part parallel to the pant transport plane.

15. The method of claim 13, wherein each fluid flow device defines a side panel transport path that in part is parallel to the pant transport plane and in part is angled with respect to the pant transport plane.

16. The method of claim 13, wherein transporting at least laterally outward portions of the side panels in the z-direction away from the pant transport plane comprises positioning the side panels within additional fluid flow devices which are disposed at an angle with respect to the pant transport plane.

17. The method of claim 13, wherein transporting at least laterally outward portions of the side panels in the z-direction away from the pant transport plane comprises sliding the side panels on a guide plate.

18. The method of claim 13, wherein the internal passageways have a flow of fluid from an entry slot toward a discharge region.

19. The method of claim 13, wherein the internal passageways each define a reference surface that is displaced from the pant transport plane in the z-direction by greater than 0 millimeters and by less than about 50 millimeters.

20. The method of claim 13, wherein the internal passageways each define a reference surface that is displaced from the pant transport plane in the z-direction by greater than about 10 millimeters and by less than about 25 millimeters.

21. The method of claim 13, further comprising transferring the side panels from the fluid flow devices to side panel transfer devices and transporting at least the laterally outward portions of the side panels on the side panel transfer devices in the z-direction toward the pant transport plane while the pant is transported in the machine direction.

22. A method for positioning side panels during manufacture of a pant, comprising:

transporting a pant in a machine direction thus defining a pant transport plane and a z-direction perpendicular to the pant transport plane, the pant comprising at least one waist region comprising opposite side panels;

positioning the side panels within fluid flow devices located on opposite sides of a machine center line, each fluid flow device comprising walls defining an internal passageway, an entry slot to the internal passageway disposed toward the machine center line, and a fluid discharge region opposite the entry slot, the walls extending in the machine direction;

creating a flow of fluid through each internal passageway from the entry slot toward the fluid discharge region; and transporting the side panels in the machine direction within the fluid flow devices while at least laterally outward portions of the side panels are displaced in the z-direction from the pant transport plane.

* * * * *